United States Patent
Kleidon et al.

(10) Patent No.: US 10,548,840 B2
(45) Date of Patent: **\*Feb. 4, 2020**

(54) METHODS AND SYSTEMS FOR FORMING STABLE DROPLETS

(71) Applicant: Ojai Energetics PBC, Ojai, CA (US)

(72) Inventors: William Kleidon, Ojai, CA (US); Justin Kirkland, Champaign, IL (US)

(73) Assignee: Ojai Energetics PBC, Ojai, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/403,325

(22) Filed: May 3, 2019

(65) Prior Publication Data

US 2019/0254969 A1    Aug. 22, 2019

Related U.S. Application Data

(63) Continuation of application No. 16/104,630, filed on Aug. 17, 2018, now Pat. No. 10,350,165, which is a
(Continued)

(51) Int. Cl.
*A61K 9/107* (2006.01)
*A61K 47/36* (2006.01)
(Continued)

(52) U.S. Cl.
CPC .......... *A61K 9/107* (2013.01); *A23L 2/39* (2013.01); *A23L 2/52* (2013.01); *A23L 33/10* (2016.08); *A23L 33/105* (2016.08); *A61K 9/5036* (2013.01); *A61K 31/05* (2013.01); *A61K 31/192* (2013.01); *A61K 31/57* (2013.01);
(Continued)

(58) Field of Classification Search
CPC ...... A61K 9/107; A61K 9/5036; A61K 47/46; A61K 47/10; A61K 47/26; A61K 31/192; A61K 47/44; A61K 31/57; A61K 31/05; A61K 47/36; A23V 2002/00;
(Continued)

(56) References Cited

U.S. PATENT DOCUMENTS 3,456,049 A   7/1969   Edward et al.
4,888,194 A   12/1989  Andersen et al.
(Continued)

FOREIGN PATENT DOCUMENTS

WO   WO-9843497 A2   10/1998
WO   WO 2012075575  *  6/2012  ............ A23L 1/48
(Continued)

OTHER PUBLICATIONS

Kim et al., (Microspheres for Drug Delivery. In: BioMEMS and Biomedical Nanotechnology. 2006. pp. 19-50) (Year: 2006).*
(Continued)

*Primary Examiner* — Jana A Hines
(74) *Attorney, Agent, or Firm* — Wilson Sonsini Goodrich and Rosati

(57) ABSTRACT

The present disclosure provides methods and systems for forming stable droplets as part of an emulsion. The emulsion may be, for example, formed by bringing an aqueous phase in contact with an oil phase at a droplet generation junction of a droplet generator. Droplets of the present disclosure may be used for holding compositions for various uses.

21 Claims, 11 Drawing Sheets

Related U.S. Application Data continuation-in-part of application No. 16/058,978, filed on Aug. 8, 2018, which is a continuation of application No. 15/452,530, filed on Mar. 7, 2017, now Pat. No. 10,080,736, which is a continuation of application No. PCT/US2015/065268, filed on Dec. 11, 2015.

(60) Provisional application No. 62/128,761, filed on Mar. 5, 2015, provisional application No. 62/091,445, filed on Dec. 12, 2014.

(51) Int. Cl.
| | |
|---|---|
| *A61K 47/46* | (2006.01) |
| *A61K 47/10* | (2017.01) |
| *A61K 47/26* | (2006.01) |
| *A61K 31/192* | (2006.01) |
| *A61K 47/44* | (2017.01) |
| *A61K 31/57* | (2006.01) |
| *A23L 33/105* | (2016.01) |
| *A23L 2/39* | (2006.01) |
| *A61K 31/05* | (2006.01) |
| *A23L 33/10* | (2016.01) |
| *C12G 3/055* | (2019.01) |
| *A23L 2/52* | (2006.01) |
| *A61K 9/50* | (2006.01) |

(52) U.S. Cl.
CPC .............. *A61K 47/10* (2013.01); *A61K 47/26* (2013.01); *A61K 47/36* (2013.01); *A61K 47/44* (2013.01); *A61K 47/46* (2013.01); *C12G 3/055* (2019.02); *A23V 2002/00* (2013.01)

(58) Field of Classification Search
CPC . A23L 33/105; A23L 2/39; A23L 2/52; A23L 33/10; C12G 3/055
See application file for complete search history.

(56) References Cited

U.S. PATENT DOCUMENTS

| | | | |
|---|---|---|---|
| 5,674,522 | A | 10/1997 | Shah et al. |
| 6,403,126 | B1 | 6/2002 | Webster et al. |
| 7,399,872 | B2 | 7/2008 | Webster et al. |
| 8,808,734 | B2 | 8/2014 | Winnicki |
| 9,095,555 | B2 | 8/2015 | Winnicki |
| 10,080,736 | B2 | 9/2018 | Kleidon et al. |
| 2004/0132621 | A1 | 7/2004 | Frisch et al. |
| 2006/0051416 | A1 | 3/2006 | Rastogi et al. |
| 2006/0269606 | A1 | 11/2006 | Gustafsson et al. |
| 2007/0065512 | A1 | 3/2007 | Dedhiya et al. |
| 2007/0298100 | A1 | 12/2007 | Barras et al. |
| 2008/0242741 | A1 | 10/2008 | Perry |
| 2008/0279940 | A1* | 11/2008 | Rigassi ............... A61K 9/1075 424/484 |
| 2009/0110674 | A1 | 4/2009 | Loizou |
| 2011/0086829 | A1 | 4/2011 | Zadini et al. |
| 2011/0236364 | A1 | 9/2011 | Bromley |
| 2012/0043242 | A1 | 2/2012 | Hospodor |
| 2012/0046351 | A1 | 2/2012 | Hospodor |
| 2012/0046352 | A1 | 2/2012 | Hospodor |
| 2012/0095088 | A1 | 4/2012 | Hospodor |
| 2012/0231083 | A1* | 9/2012 | Carley ............... A61K 9/0095 424/494 |
| 2013/0089600 | A1 | 4/2013 | Winnicki |
| 2014/0220083 | A1 | 8/2014 | Brito et al. |
| 2016/0089320 | A1 | 3/2016 | Tan |
| 2016/0143972 | A1 | 5/2016 | Stebbins et al. |
| 2017/0172977 | A1 | 6/2017 | Kleidon et al. |
| 2018/0344686 | A1 | 12/2018 | Kleidon et al. |
| 2019/0046440 | A1 | 2/2019 | Kleidon et al. |
| 2019/0076355 | A1 | 3/2019 | Kleidon et al. |

FOREIGN PATENT DOCUMENTS

| | | | |
|---|---|---|---|
| WO | WO-2012075575 A1 | 6/2012 | |
| WO | WO-2013108254 A1 | 7/2013 | |
| WO | WO 2014100231 * | 6/2014 | ........... A61K 31/352 |
| WO | WO-2014100231 A1 | 6/2014 | |
| WO | WO-2014134281 A1 | 9/2014 | |
| WO | WO-2015068052 A2 | 5/2015 | |
| WO | WO-2016018678 A1 | 2/2016 | |
| WO | WO-2016094810 A2 | 6/2016 | |

OTHER PUBLICATIONS

Afoulous, et al. Helichrysum gymnocephalum essential oil: chemical composition and cytotoxic, antimalarial and antioxidant activities, attribution of the activity origin by correlations. Molecules. Sep. 29, 2011;16(10):8273-91. doi: 10.3390/molecules16108273.

Ahmad, et al. Preclinical renal cancer chemopreventive efficacy of geraniol by modulation of multiple molecular pathways. Toxicology. Nov. 28, 2011;290(1):69-81. doi: 10.1016/j.tox.2011.08.020. Epub Sep. 3, 2011.

Ahmed, et al. Phytochemical Analysis and Anti-cancer Investigation of Bswellia serrata Bioactive Constituents In Vitro. Asian Pac J Cancer Prev. 2015;16(16):7179-88.

Ali, et al. Chemical composition, antimicrobial, antioxidant and cytotoxic activity of essential oils of Plectranthus cylindraceus and Meriandra benghalensis from Yemen. Nat Prod Commun. Aug. 2012;7(8):1099-102.

Alizadeh, et al. Essential oil composition, phenolic content, antioxidant, and antimicrobial activity of cultivated Satureja rechingeri Jamzad at different phenological stages. Z Naturforsch C. 2015;70(3-4):51-8. doi: 10.1515/znc-2014-4121.

Alonso, et al. Acclimation mechanisms elicited by sprayed abscisic acid, solar UV-B and water deficit in leaf tissues of field-grown grapevines. Plant Physiol Biochem. Jun. 2015;91:56-60. doi: 10.1016/j.plaphy.2015.03.011. Epub Apr. 8, 2015.

Anter, et al. Antigenotoxicity, cytotoxicity, and apoptosis induction by apigenin, bisabolol, and protocatechuic acid. J Med Food. Mar. 2011;14(3):276-83. doi: 10.1089/jmf.2010.0139. Epub Dec. 23, 2010.

Armaka, et al. Antiviral properties of isoborneol, a potent inhibitor of herpes simplex virus type 1. Antiviral Res. Sep. 1999;43(2):79-92.

Athikomkulchai, et al. Chemical Composition of the Essential Oil from Croton oblongifolius and its Antibacterial Activity against Propionibacterium acnes. Nat Prod Commun. Aug. 2015;10(8):1459-60.

Aydin, et al. Anticancer and antioxidant properties of terpinolene in rat brain cells. Arh Hig Rada Toksikol. Sep. 2013;64(3):415-24. doi: 10.2478/10004-1254-64-2013-2365.

Barbieri, et al. Antioxidant activity and chemical composition of essential oils of three aromatic plants from La Rioja province. Pharm Biol. Apr. 13, 2015:1-6. [Epub ahead of print].

Bedse, et al. The role of endocannabinoid signaling in the molecular mechanisms of neurodegeneration in Alzheimer's disease. J Alzheimer's Dis. 2015;43(4):1115-36. doi: 10.3233/JAD-141635

Ben Ali, et al. Investigation of Antiulcer and Antioxidant Activity of *Juniperus phoenicea* L. (1753) Essential Oil in an Experimental Rat Model. Biol Pharm Bull. 2015;38(11):1738-46. doi: 10.1248/bpb.b15-00412.

Bomfim, et al. Antitumour Activity of the Microencapsulation of Annona vepretorum Essential Oil. Basic Clin Pharmacol Toxicol. Sep. 8, 2015. doi: 10.1111/bcpt.12488. [Epub ahead of print].

Bonamin, et al. The effect of a minor constituent of essential oil from Citrus aurantium: the role of β-myrcene in preventing peptic ulcer disease. Chem Biol Interact. Apr. 5, 2014;212:11-9. doi: 10.1016/j.cbi.2014.01.009. Epub Jan. 27, 2014.

Bonifacio, et al. α-bisabolol is an effective proapoptotic agent against BCR-ABL(+) cells in synergism with Imatinib and Nilotinib. PLoS One. 2012;7(10):e46674. doi: 10.1371/journal.pone.0046674. Epub Oct. 3, 2012.

Bouajaj, et al. Antibacterial, allelopathic and antioxidant activities of essential oil of *Salvia officinalis* L. growing wild in the Atlas

(56) References Cited

OTHER PUBLICATIONS

Mountains of Morocco. Nat Prod Res. 2013;27(18):1673-6. doi: 10.1080/14786419.2012.751600. Epub Dec. 14, 2012.
Boukhatem, et al. Rose geranium essential oil as a source of new and safe anti-inflammatory drugs. Libyan J Med. Oct. 7, 2013;8:22520. doi: 10.3402/ljm.v8i0.22520.
Bounihi, et al. In Vivo Potential Anti-Inflammatory Activity of *Melissa officinalis* L. Essential Oil. Adv Pharmacol Sci. 2013;2013:101759. doi: 10.1155/2013/101759. Epub Dec. 5, 2013.
Cao, et al. The potential therapeutic effects of THC on Alzheimer's disease. J Alzheimers Dis. 2014;42(3):973-84. doi: 10.3233/JAD-140093.
Carter, et al. Cannabis and amyotrophic lateral sclerosis: hypothetical and practical applications, and a call for clinical trials. Am J Hosp Palliat Care. Aug. 2010;27(5):347-56. doi: 10.1177/1049909110369531. Epub May 3, 2010.
Cavalieri, et al. Pro-apoptotic activity of α-bisabolol in preclinical models of primary human acute leukemia cells. J Transl Med. Apr. 21, 2011;9:45. doi: 10.1186/1479-5876-9-45.
Chen, et al. Effect of Hinoki and Meniki Essential Oils on Human Autonomic Nervous System Activity and Mood States. Nat Prod Commun. Jul. 2015;10(7):1305-8.
Chen, et al. Enhancement of skin permeation of flurbiprofen via its transdermal patches using isopulegol decanoate (ISO-C10) as an absorption enhancer: pharmacokinetic and pharmacodynamic evaluation. J Pharm Pharmacol. Sep. 2015;67(9):1232-9. doi: 10.1111/jphp.12428. Epub May 21, 2015.
Choi, et al. Production of porous Calcium Phosphate (CaP) ceramics with aligned pores using ceramic/camphene-based co-extrusion. Biomater Res. Jul. 3, 2015;19:16. doi: 10.1186/s40824-015-0037-z. eCollection 2015.
Choudhary, et al. Microbial transformation of (-)-guaiol and antibacterial activity of its transformed products. J Nat Prod. May 2007;70(5):849-52. Epub Mar. 27, 2007.
Ciftci, et al. Neuroprotective effects of β-myrcene following global cerebral ischemia/reperfusion-mediated oxidative and neuronal damage in a C57BL/J6 mouse. Neurochem Res. Sep. 2014;39(9):1717-23. doi: 10.1007/s11064-014-1365-4. Epub Jun. 28, 2014.
Co-pending U.S. Appl. No. 16/104,715, filed Aug. 17, 2018.
Costa, et al. Anxiolytic-like effects of phytol: possible involvement of GABAergic transmission. Brain Res. Feb. 14, 2014;1547:34-42. doi: 10.1016/j.brainres.2013.12.003. Epub Dec. 10, 2013.
Cui, et al. Co-overexpression of geraniol-10-hydroxylase and strictosidine synthase improves anti-cancer drug camptothecin accumulation in Ophiorrhiza pumila. Sci Rep. Feb. 4, 2015;5:8227. doi: 10.1038/srep08227.
Da Silva, et al. In Vitro Antimalarial Activity of Different Inhibitors of the Plasmodial Isoprenoid Synthesis Pathway. Antimicrob Agents Chemother. Aug. 2015;59(8):5084-7. doi: 10.1128/AAC.04161-14. Epub Jun. 8, 2015.
De Alencar, et al. Chemical composition of the essential oil from the leaves of *Anaxagorea brevipes* (Annonaceae) and evaluation of its bioactivity. Nat Prod Res. Nov. 19, 2015:1-5. [Epub ahead of print].
Deng, et al. Geraniol produces antidepressant-like effects in a chronic unpredictable mild stress mice model. Physiol Behav. Dec. 1, 2015;152(Pt A):264-71. doi: 10.1016/j.physbeh.2015.10.008. Epub Oct. 8, 2015.
El-Nekeety, et al. Antioxidant properties of Thymus vulgaris oil against aflatoxin-induce oxidative stress in male rats. Toxicon. Jun. 2011;57(7-8):984-91. doi: 10.1016/j.toxicon.2011.03.021. Epub Apr. 5, 2011.
El-Sawi, et al. Chemical composition, cytotoxic activity and antimicrobial activity of essential oils of leaves and berries of *Juniperus phoenicea* L. grown in Egypt. Afr J Tradit Complement Altern Med. Jun. 10, 2007;4(4):417-26.
Ethordevic, et al. Essential oil from black currant buds as chemotaxonomy marker and antimicrobial agent. Chem Biodivers. Aug. 2014;11(8):1228-40. doi: 10.1002/cbdv.201400039.
Eubanks, et al. A Molecular Link Between the Active Component of Marijuana and Alzheimer's Disease Pathology. Mol Pharm. 2006; 3(6): 773-777.
European search report with written opinion dated Jul. 6, 2018 for EP Application No. EP15867877.
Fallon, et al. Cancer treatment-related neuropathic pain: proof of concept study with menthol-a TRPM8 agonist. Support Care Cancer. Sep. 2015;23(9):2769-77. doi: 10.1007/s00520-015-2642-8. Epub Feb. 15, 2015.
Fleischli, et al. Skin Concentrations of Topically Applied Substances in Reconstructed Human Epidermis (RHE) Compared with Human Skin Using in vivo Confocal Raman Microscopy. Chimia (Aarau). 2015;69(3):147-51. doi: 10.2533/chimia.2015.147.
Ghoran, et al. Chemical composition and antimicrobial activities of Perovskia artemisioides Boiss. essential oil. Nat Prod Res. Oct. 27, 2015:1-5. [Epub ahead of print].
Girola, et al. Camphene isolated from essential oil of *Piper cernuum* (Piperaceae) induces intrinsic apoptosis in melanoma cells and displays antitumor activity in vivo. Biochem Biophys Res Commun. Nov. 27, 2015;467(4):928-34. doi: 10.1016/j.bbrc.2015.10.041. Epub Oct. 16, 2015.
Goulart, et al. Terpenes arrest parasite development and inhibit biosynthesis of isoprenoids in Plasmodium falciparum. Antimicrob Agents Chemother. Jul. 2004;48(7):2502-9.
Gu, et al. Droplets formation and merging in two-phase flow microfluidics. Int J Mol Sci. 2011;12(4):2572-97. doi: 10.3390/ijms12042572. Epub Apr. 15, 2011.
Guleria, et al. Antioxidant and antimicrobial properties of the essential oil and extracts of Zanthoxylum alatum grown in northwestern Himalaya. ScientificWorldJournal. May 28, 2013;2013:790580. doi: 10.1155/2013/790580. Print 2013.
Hanno, et al., Green Cosmetic Surfactant from Rice: Characterization and Application. Cosmetics 2015, 2, 322-341; doi:10.3390/cosmetics2040322.
Hasan, et al. Geraniol attenuates 2-acetylaminofluorene induced oxidative stress, inflammation and apoptosis in the liver of wistar rats. Toxicol Mech Methods. Sep. 2015;25(7):559-73. doi: 10.3109/15376516.2015.1070225. Epub Sep. 12, 2015.
Heinlein, et al. Monitoring of biotransformation of hop aroma compounds in an in vitro digestion model. Food Funct. Oct. 2012;3(10):1059-67. Epub Jun. 28, 2012.
Henquet, et al. Does cannabidiol protect against the negative effects of THC? The Britsh Journal of Psychiatry. 2010; 197:259-260.
Herman, et al. Linalool Affects the Antimicrobial Efficacy of Essential Oils. Curr Microbiol. Nov. 9, 2015. [Epub ahead of print].
Hoferl, et al. Composition and Comprehensive Antioxidant Activity of Ginger (*Zingiber officinale*) Essential Oil from Ecuador. Nat Prod Commun. Jun. 2015;10(6):1085-90.
Huang, et al. Combined use of borneol or menthol with labrasol promotes penetration of baicalin through rabbit cornea in vitro. Pak J Pharm Sci. Jan. 2015;28(1):1-7.
Ibrahim, et al. Geraniol, alone and in combination with pioglitazone, ameliorates fructose-induced metabolic syndrome in rats via the modulation of both inflammatory and oxidative stress status. PLoS One. Feb. 13, 2015;10(2):e0117516. doi: 10.1371/journal.pone.0117516. eCollection 2015.
"International Search Report dated Feb. 23, 2016 for International Application No. PCT/US2015/065268.".
Iuvone, et al. Neuroprotective effect of cannabidiol, a non-psychoactive component from Cannabis sativa, on beta-amyloid-induced toxicity in PC12 cells. J Neurochem. Apr. 2004;89(1):134-41.
Jambo Superfoods. Daily Ritual—Grassfed Ghee with MCT Oil & CBD. 2015. http://www.jambosuperfoods.com/collections/featured-products/products/daily-ritual-grassfed-ghee-with-mct-oil-cbd?variant=1105135047.
Jiang et al. (+)-Borneol alleviates mechanical hyperalgesia in models of chronic inflammatory and neuropathic pain in mice. Eur J Pharmacol 757:53-58 (2015).
Judzentiene, et al. Variability, toxicity, and antioxidant activity of *Eupatorium cannabinum* (hemp agrimony) essential oils. Pharm Biol. Oct. 6, 2015:1-9. [Epub ahead of print].

(56) References Cited

OTHER PUBLICATIONS

Juergens, et al. Anti-inflammatory properties of the monoterpene 1.8-cineole: current evidence for co-medication in inflammatory airway diseases. Drug Res (Stuttg). Dec. 2014;64(12):638-46. doi: 10.1055/s-0034-1372609. Epub May 15, 2014.
Jung, et al. β-Caryophyllene potently inhibits solid tumor growth and lymph node metastasis of B16F10 melanoma cells in high-fat diet-induced obese C57BL/6N mice. Carcinogenesis. Sep. 2015;36(9):1028-39. doi: 10.1093/carcin/bgv076. Epub May 29, 2015.
Karl, et al. The therapeutic potential of the endocannabinoid system for Alzheimer's disease. Expert Opin Ther Targets. Apr. 2012;16(4):407-20. doi: 10.1517/14728222.2012.671812. Epub Mar. 27, 2012.
Kasrati, et al. Chemical characterization and insecticidal properties of essential oils from different wild populations of *Mentha suaveolens* subsp. *timija* (Brig.) Harley from Morocco. Chem Biodivers. May 2015;12(5):823-31. doi: 10.1002/cbdv.201400236.
Kaw, et al. Endothelium-derived hyperpolarizing factor, but not nitric oxide or prostacyclin release, is resistant to menadione-induced oxidative stress in the bovine coronary artery. Naunyn Schmiedebergs Arch Pharmacol. Feb. 1999;359(2):133-9.
Kim, et al. Eucalyptol suppresses matrix metalloproteinase-9 expression through an extracellular signal-regulated kinase-dependent nuclear factor-kappa B pathway to exert anti-inflammatory effects in an acute lung inflammation model. J Pharm Pharmacol. Aug. 2015;67(8):1066-74. doi: 10.1111/jphp.12407. Epub Mar. 13, 2015.
Kim, K. et al., Microspheres for Drug Delivery. In: BioMEMS and Biomedical Nanotechnology. 2006 [Retrieved on: Jan. 23, 2016], pp. 19-50. Retrieved from the internet<http://www.springer.com/cda/content/document/cda_downloaddocument/9780387255637-c2.pdf?SGWID=0-0-45-418444-p61719231>; p. 36, last paragraph; p. 37, 1st paragraph.
Kotan, et al. Screening of antibacterial activities of twenty-one oxygenated monoterpenes. Z naturforsch C. Jul.-Aug. 2007;62(7-8):507-13.
Krifa, et al. Immunomodulatory and anticancer effects of Pituranthos tortuosus essential oil. Tumour Biol. Jul. 2015;36(7):5165-70. doi: 10.1007/s13277-015-3170-3. Epub Feb. 8, 2015.
Krishnan, et al. Cannabinoids for the treatment of dementia. Cochrane Database Syst Rev. Apr. 15, 2009;(2):CD007204. doi: 10.1002/14651858.CD007204.pub2.
Krist, et al. Antimicrobial activity of nerolidol and its derivatives against airborne microbes and further biological activities. Nat Prod Commun. Jan. 2015;10(1):143-8.
Lan, et al. Effect of terpene penetration enhancer and its mechanisms on membrane fluidity and potential of HaCaT keratinocytes. Zhongguo Zhong Yao Za Zhi. Feb. 2015;40(4):643-8. English abstract only.
Laribi, et al. Coriander (*Coriandrum sativum* L.) and its bioactive constituents. Fitoterapia. Jun. 2015;103:9-26. doi: 10.1016/j.fitote.2015.03.012. Epub Mar. 14, 2015.
Liu, et al. Cannabinoids for the Treatment of Agitation and Aggression in Alzheimer's Disease. CNS Drugs. Aug. 2015;29(8):615-23. doi: 10.1007/s40263-015-0270-y.
Lone, et al. Essential oil composition of Senecio graciliflorus DC: comparative analysis of different parts and evaluation of antioxidant and cytotoxic activities. Phytomedicine. May 15, 2014;21(6):919-25. doi: 10.1016/j.phymed.2014.01.012. Epub Mar. 12, 2014.
Lotfi, et al. Cymene and Metformin treatment effect on biochemical parameters of male NMRI mice fed with high fat diet. Diabetes Metab Disord. Jun. 24, 2015;14:52. doi: 10.1186/s40200-015-0182-x. eCollection 2015.
Ma, et al. Linalool inhibits cigarette smoke-induced lung inflammation by inhibiting NF-κB activation. Int Immunopharmacol. Dec. 2015;29(2):708-13. doi: 10.1016/j.intimp.2015.09.005. Epub Oct. 1, 2015.
Malmir, et al. A new bioactive monoterpene-flavonoid from Satureja khuzistanica. Fitoterapia. Sep. 2015;105:107-12. doi: 10.1016/j.fitote.2015.06.012. Epub Jun. 16, 2015.

Marcuzzi, et al. Geraniol rescues inflammation in cellular and animal models of mevalonate kinase deficiency. In Vivo. Jan.-Feb. 2011;25(1):87-92.
Marinas, et al. Chemical Composition and Antipathogenic Activity of Artemisia annua Essential Oil from Romania. Chem Biodivers. Oct. 2015;12(10):1554-64. doi: 10.1002/cbdv.201400340.
Maroof, et al. Endocannabinoid signalling in Alzheimer's disease. Biochem Soc Trans. Dec. 2013;41(6):1583-7. doi: 10.1042/BST20130140.
Marrelli, et al. Composition, antibacterial, antioxidant and antiproliferative activities of essential oils from three *Origanum* species growing wild in Lebanon and Greece. Nat Prod Res. Jul. 15, 2015:1-5. [Epub ahead of print].
Miguel, et al. Antioxidant and Antiproliferative Activities of the Essential Oils from Thymbra capitata and *Thymus* Species Grown in Portugal. Evid Based Complement Alternat Med. 2015;2015:851721. doi: 10.1155/2015/851721. Epub Jul. 2, 2015.
Mirian, et al. Cytotoxicity and antiangiogenic effects of Rhus coriaria, Pistacia vera and Pistacia khinjuk oleoresin methanol extracts. Res Pharm Sci. May-Jun. 2015;10(3):233-240.
Mitropoulou, et al. Composition, antimicrobial, antioxidant, and antiproliferative activity of Origanum dictamnus (dittany) essential oil. Microb Ecol Health Dis. May 6, 2015;26:26543. doi: 10.3402/mehd.v26.26543. eCollection 2015.
Momcilovic, et al. In vitro effects of binuclear (η (6)-p-cymene)ruthenium(II) complex containing bridging bis(nicotinate)-polyethylene glycol ester ligand on differentiation pathways of murine Th lymphocytes activated by T cell mitogen. J Biol Inorg Chem. Apr. 2015;20(3):575-83. doi: 10.1007/s00775-015-1242-x. Epub Feb. 10, 2015.
Morgan, et al. Impact of cannabidiol on the acute memory and psychotomimetic effects of smoked cannabis: naturalistic study. The Britsh Journal of Psychiatry. 2010; 197:285-290.
Mothana, et al. GC and GC/MS analysis of essential oil composition of the endemic Soqotraen Leucas virgata Balf.f. and its antimicrobial and antioxidant activities. Int J Mol Sci. Nov. 21, 2013;14(11):23129-39. doi: 10.3390/ijms141123129.
Nam, et al. The therapeutic efficacy of α-pinene in an experimental mouse model of allergic rhinitis. Int Immunopharmacol. Nov. 2014;23(1):273-82. doi: 10.1016/j.intimp.2014.09.010. Epub Sep. 19, 2014.
Napoli, et al. Wild Sicilian rosemary: phytochemical and morphological screening and antioxidant activity evaluation of extracts and essential oils. Chem Biodivers. Jul. 2015;12(7):1075-94. doi: 10.1002/cbdv.201400274.
Nawaz, et al. Clinical efficacy of polyherbal formulation Eezpain spray for muscular pain relief. Pak J Pharm Sci. Jan. 2015;28(1):43-7.
Naz, et al. Bioactivity and chemical characterisation of Lophostemon suaveolens—an endemic Australian Aboriginal traditional medicinal plant. Nat Prod Res. May 5, 2015:1-4. [Epub ahead of print].
Notice of allowance dated Apr. 11, 2019 for U.S. Appl. No. 16/104,630.
Office action dated Apr. 30, 2019 for U.S. Appl. No. 16/104,715.
Office Action dated May 11, 217 for U.S. Appl. No. 15/452,530.
Office Action dated Sep. 27, 2017 for U.S. Appl. No. 15/452,530.
Office action dated Nov. 2, 2018 for U.S. Appl. No. 16/104,715.
Office action dated Nov. 20, 2018 for U.S. Appl. No. 16/104,630.
Ohtsubo, et al. Inhibition of the compound action potentials of frog sciatic nerves by aroma oil compounds having various chemical structures. Pharmacol Res Perspect. Mar. 2015;3(2):e00127. doi: 10.1002/prp2.127. Epub Mar. 13, 2015.
Oz, et al. Effects of monoterpenes on ion channels of excitable cells. Pharmacol Ther. Aug. 2015;152:83-97. doi: 10.1016/j.pharmthera.2015.05.006. Epub May 5, 2015.
Pardo, et al. De novo production of six key grape aroma monoterpenes by a geraniol synthase-engineered S. cerevisiae wine strain. Microb Cell Fact. Sep. 16, 2015;14:136. doi: 10.1186/s12934-015-0306-5.
Paula-Friere, et al. Evaluation of the antinociceptive activity of *Ocimum gratissimum* L. (Lamiaceae) essential oil and its isolated active principles in mice. Phytother Res. Aug. 2013;27(8):1220-4. doi: 10.1002/ptr.4845. Epub Oct. 10, 2012.

(56) References Cited

OTHER PUBLICATIONS

Paula-Friere, et al. Ocimum gratissimum Essential Oil and Its Isolated Compounds (Eugenol and Myrcene) Reduce Neuropathic Pain in Mice. Planta Med. Nov. 19, 2015. [Epub ahead of print].
Piccinelli, et al. Antihyperalgesic and antidepressive actions of (R)-(+)-limonene, α-phellandrene, and essential oil from Schinus terebinthifolius fruits in a neuropathic pain model. Nutr Neurosci. Jul. 2015;18(5):217-24. doi: 10.1179/1476830514Y.0000000119. Epub Mar. 25, 2014.
Pontin, et al. Allium sativum produces terpenes with fungistatic properties in response to infection with Sclerotium cepivorum. Phytochemistry. Jul. 2015;115:152-60. doi: 10.1016/j.phytochem. 2015.02.003. Epub Mar. 26, 2015.
Rajendran, et al. Chemical composition, antibacterial and antioxidant profile of essential oil from *Murraya koenigii* (L.) leaves. Avicenna J Phytomed. May 2014;4(3):200-14.
Rezaie, et al. Chemical composition, antioxidant and antibacterial properties of Bene (*Pistacia atlantica* subsp. mutica) hull essential oil. J Food Sci Technol. Oct. 2015;52(10):6784-90. doi: 10.1007/s13197-015-1789-0. Epub Mar. 6, 2015.
Sabogal-Guaqueta, et al. Linalool reverses neuropathological and behavioral impairments in old triple transgenic Alzheimer's mice. Neuropharmacology. Nov. 6, 2015;102:111-120. doi: 10.1016/j.neuropharm.2015.11.002. [Epub ahead of print].
Sadraei, et al. Comparison of antispasmodic effects of Dracocephalum kotschyi essential oil, limonene and α-terpineol. Res Pharm Sci. Mar.-Apr. 2015;10(2):109-16.
Salim, et al. Chemical profile, antiproliferative and antioxidant activities of rhizome oil of Zingiber anamalayanum from Western Ghats in India. Nat Prod Res. Oct. 9, 2015:0. [Epub ahead of print].
Seebaluck, et al. Medicinal plants from the genus *Acalypha* (Euphorbiaceae)—a review of their ethnopharmacology and phytochemistry. J Ethnopharmacol. Jan. 15, 2015;159:137-57. doi: 10.1016/j.jep.2014.10.040. Epub Oct. 30, 2014.
Seki, et al. Antitumor effects of α-bisabolol against pancreatic cancer. Cancer Sci. Dec. 2011;102(12):2199-205. doi: 10.1111/j.1349-7006.2011.02082.x. Epub Sep. 26, 2011.
Shah, et al. Scientific basis for the therapeutic use of *Cymbopogon citratus*, stapf (Lemon grass). J Adv Pharm Technol Res. Jan. 2011;2(1):3-8. doi: 10.4103/2231-4040.79796.
Sharma, et al. Composition and antioxidant activity of Senecio nudicaulis Wall. ex DC. (Asteraceae): a medicinal plant growing wild in Himachal Pradesh, India. Nat Prod Res. 2015;29(9):883-6. doi: 10.1080/14786419.2014.990904. Epub Dec. 17, 2014.
Sherkheli, et al.Borneol inhibits TRPA1, a proinflammatory and noxious pain-sensing cation channel. Pak J Pharm Sci. Jul. 2015;28(4):1357-63.
Shimada, et al. Characterization of three linalool synthase genes from Citrus unshiu Marc. and analysis of linalool-mediated resistance against *Xanthomonas citri* subsp. citri and Penicilium italicum in citrus leaves and fruits. Plant Sci. Dec. 2014;229:154-66. doi: 10.1016/j.plantsci.2014.09.008. Epub Sep. 22, 2014.
Siani, et al. Anti-inflammatory activity of essential oils from Syzygium cumini and Psidium guajava. Pharm Biol. Jul. 2013;51(7):881-7. doi: 10.3109/13880209.2013.768675. Epub Apr. 11, 2013.
Sieniawska, et al. Morphological Changes in the Overall *Mycobacterium tuberculosis* H37Ra Cell Shape and Cytoplasm Homogeneity due to *Mutellina purpurea* L. Essential Oil and Its Main Constituents. Med Princ Pract. Oct. 2015;24(6):527-32. doi: 10.1159/000439351. Epub Sep. 19, 2015.
Silva, et al. Gastroprotective activity of isopulegol on experimentally induced gastric lesions in mice: investigation of possible mechanisms of action. Naunyn Schmiedebergs Arch Pharmacol. Sep. 2009;380(3):233-45. doi: 10.1007/s00210-009-0429-5. Epub May 29, 2009.
Silva, et al. Ocimum basilicum: Antibacterial activity and association study with antibiotics against bacteria of clinical importance. Pharm Biol. Oct. 10, 2015:1-5. [Epub ahead of print]

Simoes, et al. Biomedical properties and potentiality of Lippia microphylla Cham. and its essential oils. J Intercult Ethnopharmacol. Jul.-Sep. 2015;4(3):256-63. doi: 10.5455/jice.20150610104841. Epub Jun. 26, 2015.
Slamenova, et al. Investigation of anti-oxidative, cytotoxic, DNA-damaging and DNA-protective effects of plant volatiles eugenol and borneol in human-derived HepG2, Caco-2 and VH10 cell lines. Mutat Res. Jun.-Jul. 2009;677(1-2):46-52. doi: 10.1016/j.mrgentox. 2009.05.016. Epub Jun. 6, 2009.
Slavchev, et al. Antimycobacterial activity generated by the amide coupling of (-)-fenchone derived aminoalcohol with cinnamic acids and analogues. Bioorg Med Chem Lett. Nov. 1, 2014;24(21):5030-3. doi: 10.1016/j.bmcl.2014.09.021. Epub Sep. 16, 2014.
Sokolova, et al. Curare-Like Camphor Derivatives and Their Biological Activity. Bioorg Khim. Mar.-Apr. 2015;41(2):203-11. English abstract only.
Sourmaghi, et al. Comparison of essential oil composition and antimicrobial activity of *Coriandrum sativum* L. extracted by hydrodistillation and microwave-assisted hydrodistillation. J Food Sci Technol. Apr. 2015;52(4):2452-7. doi: 10.1007/s13197-014-1286-x. Epub Feb. 20, 2014.
Souza, et al. Antinociceptive activity of the ethanolic extract, fractions, and aggregatin D isolated from Sinningia aggregata tubers. PLoS One. Feb. 26, 2015;10(2):e0117501. doi: 10.1371/journal.pone.0117501. eCollection 2015.
Strobel, et al. Muscodor albus E-6, an endophyte of Guazuma ulmifolia making volatile antibiotics: isolation, characterization and experimental establishment in the host plant. Microbiology. Aug. 2007;153(Pt 8):2613-20.
Su, et al. Composition and in vitro anticancer activities of the leaf essential oil of Neolitsea variabillima from Taiwan. Nat Prod Commun. Apr. 2013;8(4):531-2.
Su, et al. Composition and in-vitro cytotoxic activities of the leaf essential oil of Beilschmiedia erythrophloia from Taiwan. Nat Prod Commun. Jan. 2013;8(1):143-4.
Su, et al. Composition, in vitro Anti-inflammatory, Antioxidant and Antimicrobial Activities of Essential Oils from Leaf and Twig Parts of Cupressus cashmeriana. Nat Prod Commun. Aug. 2015;10(8):1461-4.
Supplemental materials for Vallee, et al. Pregnenolone can protect the brain from cannabis intoxication. Science. 2014; 343:94-98.
Tadtong, et al.Chemical Components of Four Essential Oils in Aromatherapy Recipe. Nat Prod Commun. Jun. 2015;10(6):1091-2.
Takaishi, et al. Inhibitory effects of monoterpenes on human TRPA1 and the structural basis of their activity. J Physiol Sci. Jan. 2014;64(1):47-57.
Takeda, S. et al. Cannabidiolic acid, a major cannabinoid in fiber-type cannabis, is an inhibitor of MDA-MB-231 breast cancer cell migration. Toxicology Letters. Nov. 15, 2012. vol. 214. No. 3. pp. 314-319: abstract.
Tenfen, et al. Chemical composition and evaluation of the antimicrobial activity of the essential oil from leaves of Eugenia platysema. Nat Prod Res. Nov. 23, 2015:1-5. [Epub ahead of print].
Terpenes. SC labs. Jun. 2014. Web Accessed Dec. 10, 2015. Printed on Apr. 7, 2017. Available at: http://sclabs.com/learn/terpenes.html.
The chemistry of essential oils, and their chemical components. 1998-2017. Accessed Dec. 10, 2015. Printed on Apr. 7, 2017. Available at: http://www.essentialoils.co.za/components.htm.
Ton, et al. Menthol Enhances the Desensitization of Human α3 β4 Nicotinic Acetylcholine Receptors. Mol Pharmacol. Aug. 2015;88(2):256-64. doi: 10.1124/mol.115.098285. Epub May 11, 2015.
Tsai, et al. Antimicrobial, antioxidant, and anti-inflammatory activities of essential oils from five selected herbs. Biosci Biotechnol Biochem. 2011;75(10):1977-83. Epub Oct. 7, 2011.
U.S. Appl. No. 15/452,530 Notice of Allowance dated May 23, 2018.
U.S. Department of health and human services. Guidance for industry estimating the maximum safe starting dose in initial clinical trials for therapeutics in adult healthy volunteers. Jul. 2015. Retrieved on: Jan. 23, 2016. pp. 1-30. Retrieve from http://www.fda.gov.ohrms/dockets/98fr/02d-0492-gdl0002.pdf; table1.

(56) References Cited

OTHER PUBLICATIONS

Vallee, et al. Pregnenolone can protect the brain from cannabis intoxication. Science. 2014;343:94-98.

Waikedre, et al. Antifungal Activity of the Essential Oils of Callitris neocaledonica and *C. sulcata* Heartwood (Cupressaceae). Chem Biodivers. Mar. 2012;9(3):644-53. doi: 10.1002/cbdv.201100229.

Wittig, et al. Geraniol Suppresses Angiogenesis by Downregulating Vascular Endothelial Growth Factor (VEGF)/VEGFR-2 Signaling. PLoS One. Jul. 8, 2015;10(7):e0131946. doi: 10.1371/journal.pone.0131946. eCollection 2015.

You, et al. Chemical Constituents and Activity of Murraya microphylla Essential Oil against Lasioderma serricorne. Nat Prod Commun. Sep. 2015;10(9):1635-8.

\* cited by examiner

METHODS AND SYSTEMS FOR FORMING STABLE DROPLETS

CROSS REFERENCE

This application is a continuation of U.S. application Ser. No. 16/104,630, filed Aug. 17, 2018, which is a continuation-in-part of U.S. patent application Ser. No. 16/058,978, filed Aug. 8, 2018, which is a continuation application of U.S. patent application Ser. No. 15/452,530, filed Mar. 7, 2017, now U.S. Pat. No. 10,080,736, which is a continuation of International Application No. PCT/US2015/065268, filed Dec. 11, 2015, which claims the benefit of U.S. Provisional Application No. 62/128,761, filed Mar. 5, 2015, and U.S. Provisional Application No. 62/091,445, filed Dec. 12, 2014, each of which applications is entirely incorporated herein by reference.

BACKGROUND

Therapeutic compositions suffer from drawbacks limiting their utility for administration to subjects. Many compositions are destroyed, broken down, or cleared by the liver, resulting in reduced delivery to the subject. Many therapeutic compositions also have low bioavailability and shelf life stability. In some instances, oil-based therapeutic compositions may be unstable in aqueous solutions, and difficult to delivery and/or administer to a subject.

SUMMARY

There remains a substantial need for compositions having increased bioavailability, increased shelf stability, reduced first pass metabolism, and other beneficial properties. Provided are methods for microencapsulating therapeutic compounds to increase bioavailability, increase shelf stability, reduce first pass metabolism, extend or modify release profiles, and increase solubility in water, such as to ease delivery and/or administration thereof to a subject. Therapeutic compositions of the present disclosure can be used to treat various diseases or conditions in subjects. Microencapsulation may involve generating a plurality of droplets in an emulsion.

In an aspect, provided is a method for generating a plurality of droplets as part of an emulsion, comprising: (a) in a droplet generator, (i) flowing an oil phase comprising one or more compositions present in an amount of at least one microgram along a first channel and (ii) flowing an aqueous phase along a second channel, towards a droplet generation junction of the first channel and the second channel; (b) at the droplet generation junction, bringing the aqueous phase in contact with the oil phase and a surfactant, to generate the emulsion comprising a plurality of droplets, wherein a droplet of the plurality of droplets comprises the one or more compositions from the oil phase, and wherein the droplet has a size less than or equal to about 1 micrometer; and (c) collecting the plurality of droplets.

In some embodiments, the plurality of droplets are water soluble.

In some embodiments, the method further comprises storing the plurality of droplets under shelf conditions for at least 1 week in a stable state. In some embodiments, the method further comprises storing the plurality of droplets under shelf conditions for at least 2 weeks in a stable state. In some embodiments, the method further comprises storing the plurality of droplets under shelf conditions for at least 1 month in a stable state.

In some embodiments, the one or more compositions in the plurality of droplets has a bioavailability of at least twice that of the one or more compositions in non-droplet-encapsulated form.

In some embodiments, the droplet generator comprises a third channel in fluid communication with the droplet generation junction, and wherein in (b) the plurality of droplets flow away from the droplet generation junction along the third channel.

In some embodiments, the droplet has a size less than or equal to about 500 nanometers. In some embodiments, the droplet has a size between about 10 nanometers and about 200 nanometers.

In some embodiments, the droplet is characterized by at least one of a sigmoidal release profile of the one or more compositions; a plasma half-life of the one or more compositions greater than twice that of the one or more compositions in non-encapsulated form; a first pass metabolism of the one or more compositions reduced by at least 50% compared to the one or more compositions in non-encapsulated form; a rate of excretion of the one or more compositions from a subject's body reduced by at least 20% compared to the one or more compositions in non-encapsulated form; and a degradation rate at an ambient temperature of at least 20° Celsius (° C.) of the one or more compositions of less than about 50% of a degradation rate of the one or more compositions in non-encapsulated form.

In some embodiments, the one or more compositions are one or more therapeutic compositions.

In some embodiments, the one or more compositions comprise at least one agent selected from the group consisting of an herb, an essential oil, a therapeutic compound, a food product, a mushroom, pregnenolone, fulvic acid, L-Theanine, Fish Oil, phenyl ethyl amine (PEA), tulsi, lemon balm, passion flower, blue lotus, cacao, maca, schizandra, Siberian ginseng, kava, skullcap, valerian, hops, California poppy, catuba, epidmedium, pao d'arco, ashwaganda, ginko, albiza, reishi, lion's mane, maitake, chaga, vitamin C, turmeric, cannabidiol (CBD), tetrahydrocannabinol (THC), bioperine, and xanthohumol.

In some embodiments, the surfactant comprises a natural surfactant or a natural oil. In some embodiments, the natural surfactant is selected from a group consisting of saponin, xylitol, and seed hull extract.

In some embodiments, the emulsion comprises a stabilizer. In some embodiments, the stabilizer is alginate.

In some embodiments, the oil phase comprises a cannabinoid compound and at least one terpene compound.

In some embodiments, the plurality of droplets has a polydispersity index of less than about 10. In some embodiments, the plurality of droplets has a polydispersity index of less than about 5. In some embodiments, the plurality of droplets has a polydispersity index of less than about 2. In some embodiments, the plurality of droplets has a polydispersity index of less than about 1.2.

An aspect of the present disclosure provides a composition comprising a plurality of microcapsules, wherein an individual microcapsule of the plurality comprises (a) at least one cannabinoid compound and (b) at least one terpene compound present in an amount of at least about one microgram.

An aspect of the present disclosure provides a composition comprising a plurality of microcapsules, wherein an individual microcapsule of the plurality comprises at least one cannabinoid compound, and wherein the microcapsules are not liposomes or micelles.

An aspect of the present disclosure provides a composition comprising a plurality of microcapsules, wherein an individual microcapsule of the plurality of microcapsules comprises at least one cannabinoid compound, and wherein the composition has a shelf half-life of at least 30 days.

An aspect of the present disclosure provides a composition comprising a plurality of microcapsules, wherein an individual microcapsule of the plurality of microcapsules comprises at least one cannabinoid compound and wherein the individual microcapsule of the plurality of microcapsules is characterized by at least one of: (a) a sigmoidal release profile of the at least one cannabinoid compound; (b) a plasma half-life of the at least one cannabinoid compound greater than twice that of the at least one cannabinoid compound in non-encapsulated form; (c) a first pass metabolism of the at least one cannabinoid compound reduced by at least 50% compared to the at least one cannabinoid compound in non-encapsulated form; (d) a rate of excretion of the at least one cannabinoid compound from a subject's body reduced by at least 20% compared to the at least one cannabinoid compound in non-encapsulated form; or (e) a degradation rate at an ambient temperature of at least 20° C. of the at least one cannabinoid compound of less than about 50% of a degradation rate of the at least one cannabinoid compound in non-encapsulated form.

In some embodiments of aspects provided herein, the at least one cannabinoid compound comprises cannabidiol (CBD). In some embodiments of aspects provided herein, the individual microcapsule of the plurality of microcapsules comprises less than 0.3% tetrahydrocannabinol (THC). In some embodiments of aspects provided herein, the composition further comprises alginate. In some embodiments of aspects provided herein, the at least one cannabinoid compound has a bioavailability of at least twice that of the at least one cannabinoid in non-encapsulated form. In some embodiments of aspects provided herein, no more than 10% of the at least one cannabinoid compound is released from the microcapsule within 1 hour after administration of the composition to a subject. In some embodiments of aspects provided herein, the at least one cannabinoid compound exists in a liquid in the individual microcapsule. In some embodiments of aspects provided herein, the composition is a solid composition.

Compositions of the present disclosure can comprise one or more herbal ingredients. Herbal ingredients can include but are not limited to: maca, he shou wu, iporuru (*Alchornea castaneifolia*), kanna (*Sceletium Tortosum*), honokiol (*Magnolia grandiflora*), Sour Jujube Seed Semen (*Ziziphi Spinosae*), Cnidium Fruit (*Fructus Cnidii*), Corydalis Rhizome (*Corydalis yanhusuo*), Albizia Bark or Flower (*Cortex albiziae*), Ginseng (*Panax ginseng*), Polygonum (*Polygoni Multiflori*), Fu ling (*Poria cocos*), Cornus Fruit (*Fructus corni*), Chinese Yam (*Rhizoma dioscoreae*), Muira puama, Dendrobium sp., Licorice Root Radix (*Glycyrrhizae Preparata*), Cordyceps (*Cordyceps sinensis*), Chinese Angelica Root (*Angelicae Sinensis*), Kratom (*Mitragyna speciosa*), Bacopa monnieri, Catuaba, Ashwaghanda, Peganum harmala, Wheat Grass, Alfalfa Grass, Oat Grass, Kamut Grass, Echinacea, Chlorella, Amla Fruit, Stinging Nettles, Carob, Mesquite, Chuchuhuasai, Clavo Huasca, Chanca Piedra, Guayusa Powder, Rhodiola rosea, Shilajit, Higenamine, Moringa (*Moringa oleifera*), Horny Goat Weed (*Epidmedium*), Astragalus, Aloe Vera, Turmeric, Pine Pollen, Cucurmine (tumeric compound), Hops, Xanthohumol (hops compound), Passion Flower, Mucuna Puriens, Tusli, Black Pepper, Bioperine (black pepper compound), Siberian Ginseng, American Ginseng, Yerba Mate, Lemon Balm, Astragulus, Kava Kava, Schizandra, Skullcap, Valerian, California Poppy, Epidmedium, Pau D'Arco, Gingko, Blue Lotus, White Lilly, and Cacao. Herbal ingredients can comprise essential oils.

Exemplary essential oils include but are not limited to: Linalool; B-Caryophyllene; B-Myrcene; D-Limonene; Humulene; a-Pinene; Ylang Ylang (*Cananga odorata*); Yarrow (*Achillea millefolium*); Violet (*Viola odorata*); Vetiver (*Vetiveria zizanoides*); Vanilla (*Vanilla plantifolia*); Tuberose (*Polianthes tuberosa*); Thyme (*Thymus vulgaris* L.); Tea Tree (*Melaleuca alternifolia*); Tangerine (*Citrus reticulata*); Spruce, Black (*Picea mariana*); Spruce (*Tsuga Canadensis*); Spikenard (*Nardostachys jatamansi*); Spearmint (*Mentha spicata*); Sandalwood (*Santalum spicatum*); Rosewood (*Aniba rosaeodora*); Rosemary Verbenone (*Rosmarinus officinalis*); Rosemary (*Rosmarinus officinalis*); Rose (*Rosa damascena*); Rose Geranium (*Pelargonium roseum*); Ravensara (*Ravensara aromatica*); Plai (*Zingiber cassumunar*) Pine Needle (*Pinus sylvestris* L.) Petitgrain (*Citrus aurantium*); Peppermint (*Mentha piperita*); Pepper, Black (*Piper nigrum* L.); Patchouli (*Pogostemon cablin*); Palo Santo (*Bursera graveolens*); Palmarosa (*Cymbopogon martini*); Osmanthus (*Osmanthus fragrans*); Oregano (*Origanum vulgare*); Orange, Sweet (*Citrus sinensis*); Oak Moss (*Evernia prunastri*); Nutmeg (*Myristica fragrans*) Niaouli (*Melaleuca viridifloria*); Neroli (aka Orange Blossom) (*Citrus aurantium*); Myrtle (*Myrtus communis*); Myrrh (*Commiphora myrrha*); Mimosa (*Acacia decurrens*); Melissa (*Melissa officinalis* L.); Marjoram, Sweet (*Origanum majorana*); Manuka (*Leptospermum scoparium*); Mandarin, Red (*Citrus deliciosa*); Mandarin (*Citrus deliciosa*); Lotus, White (*Nelumbo nucifera*); Lotus, Pink (*Nelumbo nucifera*); Lotus, Blue (*Nelumbo nucifera*); Lime (*Citrus aurantifolia*); Lily (*Lilum aurantum*); Lemongrass (*Cymbopogon citratus*); Lemon (*Citrus limonum*); Lavender (*Lavandula angustifolium*); Lavandin (*Lavandula hybrida grosso*); Kanuka (*Kunzea ericoides*); Juniper Berry (*Juniperus cummunis*); Jasmine (*Jasminum officinale*); Jasmine Abs (*Jasminum sambac*); Helichrysum (*Helichrysum italicum*); Grapefruit, White (*Citrus×paradisi*); Grapefruit, Pink (*Citrus paradisi*); Ginger (*Zingiber officinalis*); Geranium (*Pelargonium graveolens*); Geranium, Bourbon (*Pelargonium graveolens*, 'Herit'); Gardenia (*Gardenia jasminoides*); Galbanum (*Ferula galbaniflua*); Frankincense (*Boswellia carterii*); Frangipani (*Plumeria alba*); Fir Needle White (*Abies alba*); Fir Needle Siberia (*Abies siberica*); Fir Needle Canada (*Abies balsamea*); Fennel, Sweet (*Foeniculum vulgare*); Eucalyptus Smithii. Eucalyptus Radiata, Eucalyptus Globulus, Eucalyptus Citriodora, Eucalyptus Blue Mallee (*Eucalyptus polybractea*); Elemi (*Canarium luzonicum*); Dill (*Anethum graveolens*); Cypress (*Cupressus sempervirens*); Cumin (*Cuminum cyminum*); Coriander (*Coriandum sativum*); Cocoa (*Theobroma cacao*); Clove (*Eugenia caryophylatta*); Clary Sage (*Salvia sclarea*); Cistus (aka Labdanum) (*Cistus ladaniferus* L.); Cinnamon (*Cinnamomum zeylanicum*); Chamomile, Roman (*Anthemis nobilis*); Chamomile, Blue (*Matricaria chamomilla*); Celery Seed (*Apium graveolins*); Cedarwood, Western Red (*Thuja plicata*); Cedarwood, Blood (*Juniperus virginiana*); Cedarwood Atlas (*Cedrus atlantica*); Carrot Seed (*Daucus carota*); Cardamon (*Elettaria cardamomum*); Caraway Seed (*Carum carvi*); Cajeput (*Melaleuca cajuputi*); Cade (*Juniperus oxycedrus*); Birch, White (*Betula alba*); Birch, Sweet (*Betula lenta*); Bergamot (*Citrus bergamia*); Bay Laurel (*Laurus nobilis*); Basil (*Ocimum basilicum*); Basil, Holy (*Ocimum sanctum*); Basil (*Ocimum basilicum*); Balsam Poplar (*Populus balsamifera*); Balsam Peru (*Myroxylon balsamum*); Angelica (*Angelica archangelica* L.); and combinations thereof.

Compositions of the present disclosure can comprise one or more additional compounds or derivatives thereof, including but not limited to pregnenolone, MSM, fulvic acid, L-Theanine, Fish Oil, and phenylethylamine (PEA).

In some examples, a composition of the present disclosure comprises ingredients including tulsi, lemon balm, passion flower, and blue lotus. In some examples, a composition of the present disclosure comprises ingredients including cacao, maca, schizandra, and Siberian ginseng. In some examples, a composition of the present disclosure comprises ingredients including kava, skullcap, valerian, hops, and California poppy. In some examples, a composition of the present disclosure comprises ingredients including maca, catuba, epidmedium, and pao d'arco. In some examples, a composition of the present disclosure comprises ingredients including ashwaganda, ginko, and albiza. In some examples, a composition of the present disclosure comprises ingredients including reishi, lion's mane, maitake, and chaga. In some examples, a composition of the present disclosure comprises ingredients including MSM, vitamin C, turmeric, CBD oil, bioperine, and xanthohumol.

In some embodiments of aspects provided herein, the composition is formulated for oral administration to a subject. In some embodiments of aspects provided herein, the composition is a pharmaceutical composition, further comprising a pharmaceutically acceptable excipient. In some embodiments of aspects provided herein, the pharmaceutically acceptable excipient comprises at least one inorganic salt of alginate.

An aspect of the present disclosure provides a food composition comprising: (a) a food carrier; and (b) a composition of the present disclosure.

In some embodiments of aspects provided herein, said food composition is packaged as a beverage. In some embodiments of aspects provided herein, said food composition is packaged as a solid food. In some embodiments of aspects provided herein, said food composition is packaged as semi-solid food. In some embodiments of aspects provided herein, said food composition is packaged as a food product selected from the group consisting of a snack bar, cereal product, bakery product, and dairy product.

An aspect of the present disclosure provides a method of providing cannabinoid supplementation to a subject, comprising administering to the subject a composition of the present disclosure.

An aspect of the present disclosure provides a method of preparing a cannabinoid-containing composition comprising: (a) providing a solution comprising cannabinoids; and (b) micro-encapsulating said solution to form a plurality of microcapsules of a composition of the present disclosure.

An aspect of the present disclosure provides a composition suitable for oral consumption, food preparation, or topical application, comprising: (a) at least 0.04% by weight of a cannabinoid compound; and (b) a coconut product.

An aspect of the present disclosure provides a composition suitable for oral consumption, food preparation, or topical application, comprising: (a) at least 50 milligrams (mg) of a cannabinoid compound; and (b) a coconut product.

In some embodiments of aspects provided herein, said cannabinoid compound is a cannabidiol (CBD) compound. In some embodiments of aspects provided herein, said cannabidiol compound is cannabidiolic acid (CBDA). In some embodiments of aspects provided herein, said coconut product is coconut oil. In some embodiments of aspects provided herein, said cannabinoid compound is encapsulated within microcapsules. In some embodiments of aspects provided herein, said composition is suitable for oral consumption, food preparation, or topical application. In some embodiments of aspects provided herein, said composition is solid, semi-solid, gel, or liquid. In some embodiments of aspects provided herein, said composition further comprises at least 75 mg of a cannabinoid compound. In some embodiments of aspects provided herein, said composition further comprises at least 100 mg of a cannabinoid compound. In some embodiments of aspects provided herein, said composition further comprises at least 150 mg of a cannabinoid compound. In some embodiments of aspects provided herein, said composition further comprises at least 200 mg of a cannabinoid compound.

An aspect of the present disclosure provides a unit dosage comprising: (a) a food product; and (b) at least 0.04% by weight of a cannabinoid compound.

An aspect of the present disclosure provides a unit dosage comprising: (a) a food product; and (b) a cannabinoid compound, wherein said unit dosage substantially lacks a psychoactive amount of THC.

In some embodiments of aspects provided herein, said composition is suitable for consumption or use in food preparation. In some embodiments of aspects provided herein, said food product is a beverage or beverage mix. In some embodiments of aspects provided herein, said beverage mix is a chocolate beverage mix. In some embodiments of aspects provided herein, said beverage is selected from the group consisting of coconut water, tea, coffee, soft drink, alcoholic beverage, water, milk, yogurt, and combinations thereof. In some embodiments of aspects provided herein, said water in electrolyte-enriched. In some embodiments of aspects provided herein, said food product is a dairy product. In some embodiments of aspects provided herein, said dairy product is selected from the group consisting of milk, butter, cream, cheese, and ice cream. In some embodiments of aspects provided herein, said food product is a grain product. In some embodiments of aspects provided herein, said grain product is selected from the group consisting of bread, cake, pastry, pie, cereal, granola, bagel, donut, and cracker. In some embodiments of aspects provided herein, said food product is a spread. In some embodiments of aspects provided herein, said spread is nut butter or seed butter. In some embodiments of aspects provided herein, said food product is cooking oil. In some embodiments of aspects provided herein, said food product is an energy-dense or electrolyte-enriched product and wherein said food product is selected from the group consisting of energy gels, sports drinks, energy powders, energy bars, energy shots, protein powders, and protein drinks. In some embodiments of aspects provided herein, said unit dosage further comprises a fungus ingredient selected from the group consisting of reishi mushroom, chaga mushroom, maitake mushroom, oyster mushroom, and cordyceps. In some embodiments of aspects provided herein, said unit dosage further comprises an herbal ingredient including those disclosed herein. In some embodiments of aspects provided herein, at least a portion of said cannabinoid compound is in a microencapsulated form. In some embodiments of aspects provided herein, said unit dosage further comprises between about 1 milligram (mg) and about 50 mg of pregnenolone or a functional derivative thereof. In some embodiments of aspects provided herein, at least a portion of said pregnenolone or functional derivative thereof is in a microencapsulated form. The unit dosage of claim 35 or 36, further comprising terpinolene, terpineol, and linalool. In some embodiments of aspects provided herein, the plurality of microcapsules has a polydispersity index of less than about 10. In some embodiments of aspects provided herein, the plurality of microcapsules has a polydispersity index of less than about 5. In some embodiments of aspects provided herein, the plurality of microcapsules has a polydispersity index of less than about 2. In some embodiments of aspects provided herein, the plurality of microcapsules has a polydispersity index of less than about 1.2.

An aspect of the present disclosure provides a method of providing cannabinoid supplementation to a subject, comprising administering to the subject said unit dosage.

Other goals and advantages of the invention will be further appreciated and understood when considered in conjunction with the following description and accompanying drawings. While the following description may contain specific details describing particular embodiments of the invention, this should not be construed as limitations to the scope of the invention but rather as an exemplification of preferable embodiments. For each aspect of the invention, many variations are possible as suggested herein that are known to those of ordinary skill in the art. A variety of changes and modifications can be made within the scope of the invention without departing from the spirit thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings or figures (also "FIG." and "FIGS." herein), of which:

DETAILED DESCRIPTION

Figure 1A:
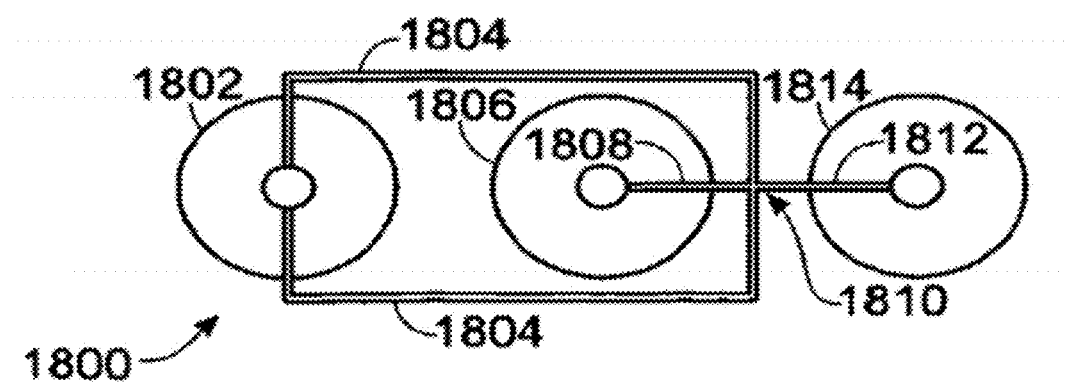
FIG. 1A shows an example of a droplet generator.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The term "about" or "nearly" as used herein refers to within +/−10%, 9%, 8%, 7%, 6%, 5%, 4%, 3%, 2%, or 1% of the designated amount.

This disclosure provides for encapsulation of therapeutic compositions, and methods for the manufacture, delivery, and use of such compositions. Therapeutic compositions can be encapsulated, including in microcapsules. Microencapsulation can provide benefits such as shelf stability, improved bioavailability, reduced first-pass metabolism, and extended or modified release profiles. Microencapsulation may involve generating a plurality of droplets in an emulsion. Microencapsulation can increase solubility of the therapeutic compositions in water (e.g., solubility of oil-based therapeutic compositions), such as to ease delivery and/or administration of the therapeutic compositions to a subject. The therapeutic compositions of the present disclosure can comprise cannabinoids, terpenes, essential oils, and other desirable compounds.

In one embodiment, the present invention provides a composition comprising a plurality of microcapsules, wherein an individual microcapsule of the plurality comprises one or more therapeutic compositions present in an amount of at least about one microgram. In another embodiment, the present invention provides a composition comprising a plurality of microcapsules, wherein an individual microcapsule of the plurality comprises one or more therapeutic compositions, and wherein the microcapsules are not liposomes or micelles. In another embodiment, the present invention provides a composition comprising a plurality of microcapsules, wherein an individual microcapsule of the plurality of microcapsules comprises one or more therapeutic compositions, and wherein the composition has a shelf half-life of at least 30 days. In other embodiments, the present invention provides food products that are rich in therapeutic compositions.

Microfluidic Encapsulation and Delivery

The compositions of the present disclosure can comprise microcapsules. Microcapsules can comprise components discussed elsewhere in this disclosure, such as a mushroom, fulvic acid, L-Theanine, Fish Oil, pregnenolone, phenyl ethyl amine (PEA), tulsi, lemon balm, passion flower, terpene compounds, blue lotus, cacao, maca, schizandra, Siberian ginseng, kava, skullcap, valerian, hops, California poppy, catuba, epidmedium, pao d'arco, ashwaganda, ginko, albiza, reishi, lion's mane, maitake, chaga, vitamin C, turmeric, cannabinoid compounds, cannabidiol (CBD), tetrahydrocannabinol (THC), bioperine, and xanthohumol oil-based compounds, and others, in microencapsulated form. In some cases, compositions can be encapsulated without the use of liposomes. In some cases, compositions can be encapsulated without the use of micelles. In some cases, compositions can be encapsulated without the use of liposomes or micelles. Compounds of the composition can exist within a microcapsule in forms including but not limited to liquid, gel, semi-solid, and solid. Microcapsules of compositions disclosed herein can further be processed into forms including but not limited to solids, powders, liquids, suspensions, gels, tablets, foods, lotions, cosmetics, and other forms discussed in this disclosure.

Microencapsulation can be performed with a microencapsulation device, including microfluidic droplet generation or encapsulation devices. An exemplary microencapsulation device is described, for example, in U.S. Pat. No. 7,482,152, incorporated here by reference in its entirety. Microfluidic droplets or emulsions can be generated by flow of a fluid to be encapsulated with an immiscible carrier fluid. For example, an oil fluid to be encapsulated can be flowed with an aqueous carrier fluid, or an aqueous fluid to be encapsulated can be flowed with an oil carrier fluid. Air can also be used as a fluid. Microfluidic droplet generators useful for microencapsulation include those employing co-flowing streams, cross-flowing streams (e.g., flow of streams at a T-junction), flow focusing, flow through perforated plates, and flow through nozzles. Droplet size can be controlled by parameters including device geometry, relative flow rates of the fluid streams, and operating pressure.

FIG. 1A shows an example of a droplet generator. In configuration 1800, a first phase (e.g., oil) from a first fluid chamber 1802 is transferred through two branches of a fluid channel section 1804. The first phase from the first fluid chamber 1802 intersects with a second phase (e.g., aqueous phase) from a second fluid chamber 1806, which is transferred along a fluid channel section 1808 to an intersection 1810 with the fluid channel section 1804. For example, the first phase from the first fluid chamber 1802 arrives at intersection 1810 from two different and substantially opposite directions, whereas the second phase arrives at the intersection along only a single path that is substantially perpendicular to both directions of travel of the arriving first phase fluid. At intersection 1810, droplets in the second phase are generated in a first phase background (e.g., a water-in-oil emulsion) and transferred along a fluid channel section 1812 to a third fluid chamber 1814, where the emulsion can be temporarily stored and/or transferred to another location. The phases can be reversed, for example, such that the droplets in the first phase are generated in a second phase background (e.g., an oil-in-water emulsion).

Figure 1B:
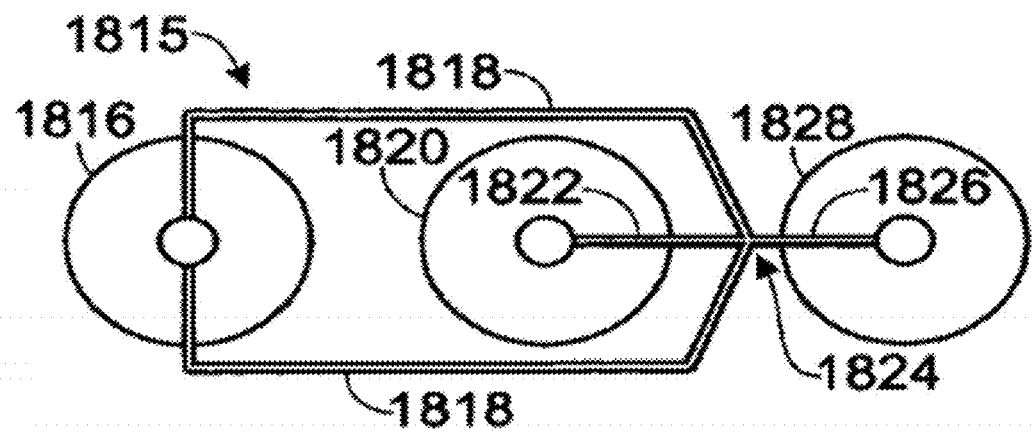
FIG. 1B shows another example of a droplet generator.

FIG. 1B shows another example of a droplet generator. In configuration 1815, a first phase (e.g., oil) from a first fluid chamber 1816 is transferred through two branches of a fluid channel section 1818. Fluid channel section 1818 intersects with a fluid channel section 1822 that transfers a second phase (e.g., aqueous) fluid from a second fluid chamber 1820, at intersection 1824. As in configuration 1800 of FIG. 1A, the first phase from the first fluid chamber 1816 arrives at intersection 1810 from two different directions, but unlike in configuration 1800, the fluid does not arrive from substantially opposite (antiparallel) directions. Rather, the branches of channel section 1818 each intersect channel section 1822 at a non-perpendicular angle, which is depicted as approximately 60 degrees in FIG. 1B. In general, configuration 1815 may include first phase fluid channels that intersect a second phase fluid channel at any desired angle or angles. The first phase fluid flowing through channel sections 1818 and the second phase fluid flowing through channel section 1822 can combine to form an emulsion of droplets in the second phase suspended in a first phase background (e.g., water-in-oil emulsion). As in the case of configuration 1800, the droplets then may be transferred along a fluid channel section 1826 to a third fluid chamber 1828, for storage and/or transfer to another location. The phases can be reversed, for example, such that the droplets in the first phase are generated in a second phase background (e.g., an oil-in-water emulsion).

Figure 1C:
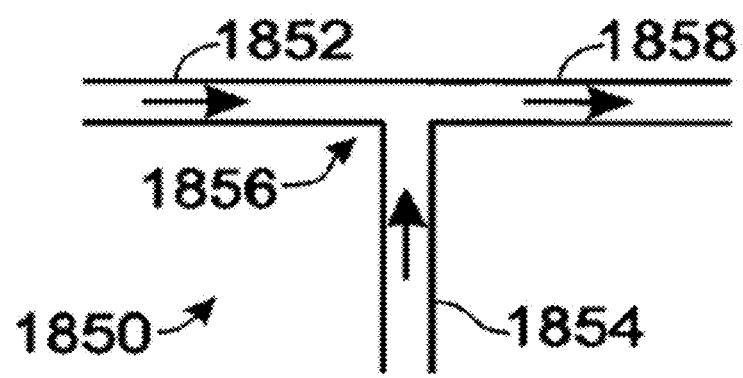
FIG. 1C shows an example of a microfluidic structure.

FIG. 1C shows an example of a microfluidic structure. The arrows within the depicted fluid channels indicate the direction of fluid flow within each channel. Although fluid chambers for receiving and/or storing oil, water, and any generated emulsion are not depicted, these chambers or at least some source of oil and aqueous fluid would be present in a cartridge containing any of the depicted configurations. The fluid channels and any associated chambers may be formed by any suitable method, such as injection molding complementary sections of thermoplastic as described previously. In a T-junction configuration 1850, a first phase fluid traveling along channel 1852 intersects with a second phase fluid traveling along channel 1854 at intersection 1856, to produce second phase-in-first phase emulsions (e.g., water-in-oil, oil-in-water, etc.) that travels along outgoing fluid channel 1858. Droplets formed in the T-junction configuration 1850 may be formed primarily by a shear mechanism rather than primarily by a compression mechanism. However, droplet formation may depend on many factors, including the channel diameters, fluid velocities, and fluid viscosities.

Microencapsulation can be performed at a range of operating parameters, such as different flow rates or pressures. Microencapsulation can be conducted at a pressure of at least about 10 pounds per square inch (psi), 20 psi, 30 psi, 40 psi, 50 psi, 60 psi, 70 psi, 80 psi, 90 psi, 100 psi, 200 psi, 300 psi, 400 psi, 500 psi, 600 psi, 700 psi, 800 psi, 900 psi, 1000 psi, 2000 psi, 3000 psi, 4000 psi, 5000 psi, 6000 psi, 7000 psi, 8000 psi, 9000 psi, 10000 psi, 15000 psi, 20000 psi, 25000 psi, 30000 psi, 35000 psi, 40000 psi, 45000 psi, 50000 psi, or more. Microencapsulation can be conducted at a pressure of at most about 10 pounds per square inch (psi), 20 psi, 30 psi, 40 psi, 50 psi, 60 psi, 70 psi, 80 psi, 90 psi, 100 psi, 200 psi, 300 psi, 400 psi, 500 psi, 600 psi, 700 psi, 800 psi, 900 psi, 1000 psi, 2000 psi, 3000 psi, 4000 psi, 5000 psi, 6000 psi, 7000 psi, 8000 psi, 9000 psi, 10000 psi, 15000 psi, 20000 psi, 25000 psi, 30000 psi, 35000 psi, 40000 psi, 45000 psi, or 50000 psi. Microencapsulation can be conducted at a pressure of about 10 pounds per square inch (psi), 20 psi, 30 psi, 40 psi, 50 psi, 60 psi, 70 psi, 80 psi, 90 psi, 100 psi, 200 psi, 300 psi, 400 psi, 500 psi, 600 psi, 700 psi, 800 psi, 900 psi, 1000 psi, 2000 psi, 3000 psi, 4000 psi, 5000 psi, 6000 psi, 7000 psi, 8000 psi, 9000 psi, 10000 psi, 15000 psi, 20000 psi, 25000 psi, 30000 psi, 35000 psi, 40000 psi, 45000 psi, 50000 psi, or more. Microencapsulation can be conducted at a flow rate of at least about 1 milliliter per minute (mL/min), 2 mL/min 3 mL/min, 4 mL/min, 5 mL/min, 6 mL/min, 7 mL/min, 8 mL/min, 9 mL/min, 10 mL/min, 20 mL/min, 30 mL/min, 40 mL/min, 50 mL/min, 60 mL/min, 70 mL/min, 80 mL/min, 90 mL/min, 100 mL/min, 110 mL/min, 120 mL/min, 130 mL/min, 140 mL/min, 150 mL/min, 160 mL/min, 170 mL/min, 180 mL/min, 190 mL/min, 200 mL/min, 210 mL/min, 220 mL/min, 230 mL/min, 240 mL/min, 250 mL/min, 260 mL/min, 270 mL/min, 280 mL/min, 290 mL/min, 300 mL/min, 310 mL/min, 320 mL/min, 330 mL/min, 340 mL/min, 350 mL/min, 360 mL/min, 370 mL/min, 380 mL/min, 390 mL/min, 400 mL/min, 410 mL/min, 420 mL/min, 430 mL/min, 440 mL/min, 450 mL/min, 460 mL/min, 470 mL/min, 480 mL/min, 490 mL/min, 500 mL/min, or more. Microencapsulation can be conducted at a flow rate of at most about 1 milliliter per minute (mL/min), 2 mL/min 3 mL/min, 4 mL/min, 5 mL/min, 6 mL/min, 7 mL/min, 8 mL/min, 9 mL/min, 10 mL/min, 20 mL/min, 30 mL/min, 40 mL/min, 50 mL/min, 60 mL/min, 70 mL/min, 80 mL/min, 90 mL/min, 100 mL/min, 110 mL/min, 120 mL/min, 130 mL/min, 140 mL/min, 150 mL/min, 160 mL/min, 170 mL/min, 180 mL/min, 190 mL/min, 200 mL/min, 210 mL/min, 220 mL/min, 230 mL/min, 240 mL/min, 250 mL/min, 260 mL/min, 270 mL/min, 280 mL/min, 290 mL/min, 300 mL/min, 310 mL/min, 320 mL/min, 330 mL/min, 340 mL/min, 350 mL/min, 360 mL/min, 370 mL/min, 380 mL/min, 390 mL/min, 400 mL/min, 410 mL/min, 420 mL/min, 430 mL/min, 440 mL/min, 450 mL/min, 460 mL/min, 470 mL/min, 480 mL/min, 490 mL/min, or 500 mL/min. Microencapsulation can be conducted at a flow rate of about 1 milliliter per minute (mL/min), 2 mL/min 3 mL/min, 4 mL/min, 5 mL/min, 6 mL/min, 7 mL/min, 8 mL/min, 9 mL/min, 10 mL/min, 20 mL/min, 30 mL/min, 40 mL/min, 50 mL/min, 60 mL/min, 70 mL/min, 80 mL/min, 90 mL/min, 100 mL/min, 110 mL/min, 120 mL/min, 130 mL/min, 140 mL/min, 150 mL/min, 160 mL/min, 170 mL/min, 180 mL/min, 190 mL/min, 200 mL/min, 210 mL/min, 220 mL/min, 230 mL/min, 240 mL/min, 250 mL/min, 260 mL/min, 270 mL/min, 280 mL/min, 290 mL/min, 300 mL/min, 310 mL/min, 320 mL/min, 330 mL/min, 340 mL/min, 350 mL/min, 360 mL/min, 370 mL/min, 380 mL/min, 390 mL/min, 400 mL/min, 410 mL/min, 420 mL/min, 430 mL/min, 440 mL/min, 450 mL/min, 460 mL/min, 470 mL/min, 480 mL/min, 490 mL/min, 500 mL/min, or more.

Droplet generators can employ multiple parallel droplet generation operations in parallel. For example, a droplet generator (e.g., a plate, a device with channels) can employ at least 1, 2, 3, 4, 5, 6, 7, 8, 9, 10, 15, 20, 25, 30, 35, 40, 45, 50, 55, 60, 65, 70, 75, 80, 85, 90, 95, 100, or more droplet generating features (e.g., holes, channels, nozzles). A droplet generator can employ at most 1, 2, 3, 4, 5, 6, 7, 8, 9, 10, 15, 20, 25, 30, 35, 40, 45, 50, 55, 60, 65, 70, 75, 80, 85, 90, 95, or 100 droplet generating features. A droplet generator can employ about 1, 2, 3, 4, 5, 6, 7, 8, 9, 10, 15, 20, 25, 30, 35, 40, 45, 50, 55, 60, 65, 70, 75, 80, 85, 90, 95, 100, or more droplet generating features.

Microencapsulation can be performed via an emulsification process. For example, compositions can be emulsified in a mixer, such as an agitator, impeller, centrifugal mixer, or high-shear mixer. High-shear mixers can include batch high-shear mixers and inline high-shear mixers (e.g., rotor-stator mixers). Emulsification can also be conducted without a mixer, by combining fluids thermodynamically favored to form an emulsion, optionally with the aid of one or more emulsifiers or surfactants.

Microencapsulation processes can be conducted with the aid of one or more emulsifiers or surfactants. Emulsifiers and surfactants can include but are not limited to saponins (e.g., quillaja tree extract such as Q-NATURALE®, yucca extract), lecithin, soy lecithin, mustard seed hull extract, sodium stearoyl lactylate, polysorbate 20, and combinations thereof.

Microcapsules can comprise one or more stabilizers or gelling agents, which can be used to stabilize a microcapsule or emulsion. Stabilizers or gelling agents can include but are not limited to alginate (also algin or alginic acid) and agar. Alginate can be used in a variety of forms, including but not limited to inorganic salts such as sodium alginate, potassium alginate, calcium alginate, and combinations thereof. Alginate can be derived from sources such as seaweed (e.g., *Macrocystis pyrifera, Ascophyllum nodosum, Laminaria* spp.) or bacteria (e.g., *Pseudomonas* spp., *Azotobacter* spp.). Cross-linking agents or solutions, such as calcium chloride, can be used to stabilize or gel microcapsules.

Microcapsules can be characterized by a size (e.g., a diameter). The microcapsule size can be about 0.154 micrometers. The microcapsule size can be less than or equal to about 0.154 micrometers. The microcapsule size can be greater than or equal to about 0.154 micrometers. The microcapsule size can be about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, 55, 60, 65, 70, 75, 80, 85, 90, 95, 100, 150, 200, 250, 300, 350, 400, 450, or 500 micrometers. The microcapsule size can be less than or equal to about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, 55, 60, 65, 70, 75, 80, 85, 90, 95, 100, 150, 200, 250, 300, 350, 400, 450, or 500 micrometers. The microcapsule size can be greater than or equal to about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, 55, 60, 65, 70, 75, 80, 85, 90, 95, 100, 150, 200, 250, 300, 350, 400, 450, or 500 micrometers. The microcapsule size can be from about 0.1 to about 0.2 micrometers. The microcapsule size can be from about 0.05 to about 0.25 micrometers. The microcapsule size can be from about 0.05 to about 0.55 micrometers. The microcapsule size can be from about 0.05 to about 1 micrometers. The size distribution in a population of microcapsules can be homogeneous or substantially homogeneous. For example, a population of microcapsules can be characterized by dispersity, or polydispersity index (PDI), of less than or equal to about 20, 19, 18, 17, 16, 16, 15, 14, 13, 12, 11, 10, 9, 8, 7, 6, 5, 4.9, 4.8, 4.7, 4.6, 4.5, 4.4, 4.3, 4.2, 4.1, 4.0, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2.0, 1.9, 1.8, 1.7, 1.6, 1.5, 1.45, 1.40, 1.35, 1.30, 1.25, 1.20, 1.15, 1.14, 1.13, 1.12, 1.11, 1.10, 1.09, 1.08, 1.07, 1.06, 1.05, 1.04, 1.03, 1.02, 1.01, or 1.00.

Compositions

Therapeutic compositions of the present disclosure may comprise a variety of compounds, such as a mushroom, fulvic acid, L-Theanine, Fish Oil, pregnenolone, phenyl ethyl amine (PEA), tulsi, lemon balm, passion flower, terpene compounds, blue lotus, cacao, maca, schizandra, Siberian ginseng, kava, skullcap, valerian, hops, California poppy, catuba, epidmedium, pao d'arco, ashwaganda, ginko, albiza, reishi, lion's mane, maitake, chaga, vitamin C, turmeric, cannabinoid compounds, cannabidiol (CBD), tetrahydrocannabinol (THC), bioperine, xanthohumol oil-based compounds, and others, and/or a combination thereof. Cannabinoids utilized in the compositions disclosed herein include but are not limited to cannabigerol-type (CBG), cannabigerolic acid (CBGA), cannabigerolic acid monomethylether (CBGAM), cannabigerol monomethyl ether (CBGM), cannabichromene-type (CBC), cannabichromanon (CBCN), cannabichromenic acid (CBCA), cannabichromevarin-type (CBCV), cannabichromevarinic acid (CBCVA), cannabidiol-type (CBD), tetrahydrocannabinol-type (THC), iso-tetrahydrocannabinol-type (iso-THC), cannabinol-type (CBN), cannabinolic acid (CBNA), cannabinol methylether (CBNM), cannabinol-$C_4$ (CBN-$C_4$), cannabinol-$C_2$ (CBN-$C_2$), cannabiorcol (CBN-$C_1$), cannabinodiol (CBND), cannabielsoin-type (CBE), cannabielsoic acid A (CBEA-A), cannabielsoic acid B (CBEA-B), cannabicyclol-type (CBL), cannabicyclolic acid (CBLA), cannabicyclovarin (CBLV), cannabicitran-type (CBT), cannabitriol, cannabitriolvarin (CBTV), ethoxy-cannabitiolvarin (CBTVE), cannabivarin-type (CBV), cannabinodivarin (CBVD), tetrahydrocannabivarin-type (THCV), cannabidivarin-type (CBDV), cannabigerovarin-type (CBGV), cannabigerovarinic acid (CBGVA), cannabifuran (CBF), dehydrocannabifuran (DCBF), and cannabiripsol (CBR) cannabinoids.

Cannabinoids used in compositions of the present disclosure can be derived from various sources, including but not limited to hemp (e.g. hemp stalk, hemp stem, hemp seed), cannabis (e.g., cannabis flower, cannabis leaf, cannabis stalk, cannabis stem, cannabis seed), *Echinacea purpurea*, *Echinacea angustifolia*, *Echinacea pallida*, *Acmella oleracea*, *Helichrysum umbraculigerum*, *Radula marginata*, kava, black truffle, *Syzygium aromaticum* (cloves), *Rosmarinus oficinalis*, basil, oregano, black pepper, lavender, true cinnamon, malabathrum, *cananga odorata*, *copaifera* spp., and hops.

Encapsulated cannabinoids can be present in a quantity of at least about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, or 50 micrograms per microcapsule. Encapsulated cannabinoids can be present in a quantity of at most about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, or 50 micrograms per microcapsule. Encapsulated cannabinoids can be present in a quantity of about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, or 50 micrograms per microcapsule. Encapsulated cannabinoids can be present in a quantity of from about 1 to about 10 micrograms per microcapsule. Encapsulated cannabinoids can be present in a quantity of at least about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% by weight of a microcapsule. Encapsulated cannabinoids can be present in a quantity of at most about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% by weight of a microcapsule. Encapsulated cannabinoids can be present in a quantity of about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% by weight of a microcapsule.

Cannabinoids can be present in a product, such as a food product, in a quantity of at least about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 150, 200, 250, 300, 350, 400, 450, or 500 milligrams (mg). Cannabinoids can be present in a product, such as a food product, in a quantity of at most about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 150, 200, 250, 300, 350, 400, 450, or 500 milligrams (mg). Cannabinoids can be present in a product, such as a food product, in a quantity of about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 150, 200, 250, 300, 350, 400, 450, or 500 milligrams (mg). Cannabinoids can be present in a product, such as a food product, in a quantity of from about 50 to about 150 milligrams. Cannabinoids can be present in a product, such as a food product, in a quantity of at least about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% by weight of the product. Cannabinoids can be present in a product, such as a food product, in a quantity of at most about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% by weight of the product. Cannabinoids can be present in a product, such as a food product, in a quantity of about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% by weight of the product.

The cannabinoids of the compositions disclosed herein can comprise cannabidiol-class compounds, including but not limited to cannabidiol (CBD), cannabidiolic acid (CBDA), cannabidiol monomethylether (CBDM), cannabidiol-$C_4$ (CBD-$C_4$), cannabidivarin (CBDV), cannabidivarinic acid (CBDVA), cannabidiorcol (CBD-$C_1$), and combinations thereof. CBD can comprise delta-1-cannabidiol, delta-2-cannabidiol, delta-3-cannabidiol, delta-3,7-cannabidiol, delta-4-cannabidiol, delta-5-cannabidiol, delta-6-cannabidiol, and combinations thereof.

Encapsulated cannabidiol compounds can be present in a quantity of at least about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, or 50 micrograms per microcapsule. Encapsulated cannabidiol compounds can be present in a quantity of at most about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, or 50 micrograms per microcapsule. Encapsulated cannabidiol compounds can be present in a quantity of about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, or 50 micrograms per microcapsule. Encapsulated cannabidiol compounds can be present in a quantity of from about 1 to about 10 micrograms per microcapsule. Encapsulated cannabidiol compounds can be present in a quantity of at least about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% by weight of a microcapsule. Encapsulated cannabidiol compounds can be present in a quantity of at most about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% by weight of a microcapsule. Encapsulated cannabidiol compounds can be present in a quantity of about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% by weight of a microcapsule.

Cannabidiol compounds can be present in a product, such as a food product, in a quantity of at least about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 150, 200, 250, 300, 350, 400, 450, or 500 milligrams (mg). Cannabidiol compounds can be present in a product, such as a food product, in a quantity of at most about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 150, 200, 250, 300, 350, 400, 450, or 500 milligrams (mg). Cannabidiol compounds can be present in a product, such as a food product, in a quantity of about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 150, 200, 250, 300, 350, 400, 450, or 500 milligrams (mg). Cannabidiol compounds can be present in a product, such as a food product, in a quantity of from about 50 to about 150 milligrams. Cannabidiol compounds can be present in a product, such as a food product, in a quantity of at least about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% by weight of the product. Cannabidiol compounds can be present in a product, such as a food product, in a quantity of at most about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% by weight of the product. Cannabidiol compounds can be present in a product, such as a food product, in a quantity of about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% by weight of the product.

The compositions of the present disclosure can comprise tetrahydrocannabinol (THC) as a type of cannabinoids. THC can comprise delta-9-THC, delta-8-THC, and combinations thereof. THC can comprise delta-6a,7-tetrahydrocannabinol, delta-7-tetrahydrocannabinol, delta-8-tetrahydrocannabinol, delta-9,11-tetrahydrocannabinol, delta-9-tetrahydrocannabinol, delta-10-tetrahydrocannabinol, delta-6a, 10a-tetrahydrocannabinol, and combinations thereof. Delta-9-tetrahydrocannabinol can comprise stereoisomers including (6aR, 10aR)-delta-9-tetrahydrocannabinol, (6aS,10aR)-delta-9-tetrahydrocannabinol, (6aS,10aS)-delta-9-tetrahydrocannabinol, (6aR,10aS)-delta-9-tetrahydrocannabinol, and combinations thereof.

In cases where the compositions comprise microcapsules, THC compounds can be present in a quantity of at least about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, or 50 micrograms per microcapsule. Encapsulated THC compounds can be present in a quantity of at most about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, or 50 micrograms per microcapsule. Encapsulated THC compounds can be present in a quantity of from about 1 to about 10 micrograms per microcapsule. Encapsulated THC compounds can be present in a quantity of about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, or 50 micrograms per microcapsule. Encapsulated THC compounds can be present in a quantity of at least about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% by weight of a microcapsule. Encapsulated THC compounds can be present in a quantity of at most about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% by weight of a microcapsule. Encapsulated THC compounds can be present in a quantity of about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% by weight of a microcapsule.

THC compounds can be present in a product, such as a food product, in a quantity of at least about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 150, 200, 250, 300, 350, 400, 450, or 500 milligrams (mg). THC compounds can be present in a product, such as a food product, in a quantity of at most about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 150, 200, 250, 300, 350, 400, 450, or 500 milligrams (mg). THC compounds can be present in a product, such as a food product, in a quantity of about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 150, 200, 250, 300, 350, 400, 450, or 500 milligrams (mg). THC compounds can be present in a product, such as a food product, in a quantity of from about 50 to about 150 milligrams. THC compounds can be present in a product, such as a food product, in a quantity of at least about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% by weight of the product. THC compounds can be present in a product, such as a food product, in a quantity of at most about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% by weight of the product. THC compounds can be present in a product, such as a food product, in a quantity of about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% by weight of the product.

In some cases, a composition of the present disclosure does not contain a psychoactive amount of THC. For example, cannabinoids in compositions of the present disclosure can contain less than 100%, 90%, 80%, 70%, 60%, 50%, 40%, 30%, 20%, 10%, 5%, 1%, 0.7%, 0.5%, 0.3%, or 0.1% THC relative to the total quantity of cannabinoid compounds. In some cases, the ratio of a non-THC cannabinoid (e.g., cannabidiol) to THC in a composition of the present disclosure is greater than or equal to about 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 25:1, 30:1, 35:1, 40:1, 45:1, 50:1, or 100:1. In some cases, compositions of the present disclosure contain less than 0.3% THC.

The compositions of the present disclosure can comprise one or more terpene compounds, including but not limited to terpenoids such as monoterpenoids, sesquiterpenoids, diterpenoids, and triterpenoids. Terpenes can be acyclic, monocyclic, or polycyclic. Terpenes can include but are not limited to myrcene, limonene, linalool, trans-ocimene, cis-ocimene, alpha-pinene, beta-pinene, alpha-humulene (alpha-caryophyllene), beta-caryophyllene, delta-3-carene, trans-gamma-bisabolene, cis-gamma-bisabolene, trans-alpha-farnesene, cis-beta-farnesene, beta-fenchol, beta-phellandrene, guajol, alpha-gualene, alpha-eudesmol, beta-eudesmol, gamma-eudesmol, terpinolene, alpha-selinene, beta-selinene, alpha-terpineol, fenchone, camphene, cis-sabinene hydrate, alpha-trans-bergamotene, alpha-cis-bergamotene, borneol, gamma-curcumene, alpha-thujene, epi-alpha-bisabolol, ipsdienol, alpha-ylangene, beta-elemene, gamma-muurolene, alpha-cadinene, alpha-longipinene, caryophyllene oxide, and combinations thereof.

Encapsulated terpenes can be present in a quantity of at least about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, or 50 micrograms per microcapsule. Encapsulated terpenes can be present in a quantity of at most about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, or 50 micrograms per microcapsule. Encapsulated terpenes can be present in a quantity of about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, or 50 micrograms per microcapsule. Encapsulated terpene compounds can be present in a quantity of from about 1 to about 10 micrograms per microcapsule. Encapsulated terpenes can be present in a quantity of at least about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% by weight of a microcapsule. Encapsulated terpenes can be present in a quantity of at most about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% by weight of a microcapsule. Encapsulated terpenes can be present in a quantity of about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% by weight of a microcapsule.

Terpene compounds can be present in a product, such as a food product, in a quantity of at least about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 150, 200, 250, 300, 350, 400, 450, or 500 milligrams (mg). Terpene compounds can be present in a product, such as a food product, in a quantity of at most about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 150, 200, 250, 300, 350, 400, 450, or 500 milligrams (mg). Terpene compounds can be present in a product, such as a food product, in a quantity of about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 150, 200, 250, 300, 350, 400, 450, or 500 milligrams (mg). Terpene compounds can be present in a product, such as a food product, in a quantity of from about 50 to about 150 milligrams. Terpene compounds can be present in a product, such as a food product, in a quantity of at least about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% by weight of the product. Terpene compounds can be present in a product, such as a food product, in a quantity of at most about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% by weight of the product. Terpene compounds can be present in a product, such as a food product, in a quantity of about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, or 50% by weight of the product.

The compositions of the present disclosure can be enriched in cannabinoids compared to hemp oil. For example, a composition can comprise hemp oil and cannabinoids from plant sources such as extracts (e.g., hemp extract) and essential oils. A composition can comprise about 0%, 10%, 20%, 30%, 40%, 50%, 60%, 70%, 80%, 90%, 100%, 200%, 300%, 400%, 500%, 600%, 700%, 800%, 900%, or 1000% greater concentration of cannabinoids compared to hemp oil.

The compositions of the present disclosure can be enriched in cannabidiol compounds compared to hemp oil. For example, a composition can comprise hemp oil and cannabidiol compounds from plant sources such as extracts (e.g., hemp extract) and essential oils. A composition can comprise about 0%, 10%, 20%, 30%, 40%, 50%, 60%, 70%, 80%, 90%, 100%, 200%, 300%, 400%, 500%, 600%, 700%, 800%, 900%, or 1000% greater concentration of cannabidiol compounds compared to hemp oil.

The compositions of the present disclosure can be enriched in THC compounds compared to hemp oil. For example, a composition can comprise hemp oil and THC compounds from plant sources such as extracts (e.g., hemp extract) and essential oils. A composition can comprise about 0%, 10%, 20%, 30%, 40%, 50%, 60%, 70%, 80%, 90%, 100%, 200%, 300%, 400%, 500%, 600%, 700%, 800%, 900%, or 1000% greater concentration of THC compounds compared to hemp oil.

The compositions of the present disclosure can be enriched in terpenes compared to hemp oil. For example, a composition can comprise hemp oil and terpenes from plant sources such as extracts (e.g., hemp extract) and essential oils. A composition can comprise about 0%, 10%, 20%, 30%, 40%, 50%, 60%, 70%, 80%, 90%, 100%, 200%, 300%, 400%, 500%, 600%, 700%, 800%, 900%, or 1000% greater concentration of terpenes compared to hemp oil.

Compounds included in the compositions of the present disclosure can be derived from various sources. Compound sources can be natural, such as plant extracts or essential oils. Compounds in the compositions of the present disclosure can be derived from hemp oil, including cannabinoid compounds, THC compounds, and terpene compounds. Compounds in the compositions of the present disclosure can be derived from essential oils, including but not limited to those essential oils discussed further in this disclosure.

These compounds can include cannabinoid compounds and terpene compounds. In some cases, all the compounds or ingredients in a composition are natural or naturally-derived. In some cases, all the compounds or ingredients in a composition are vegetarian. In some cases, all the compounds or ingredients in a composition are vegan.

Terpenes and/or essential oils in compositions of the present disclosure can be selected to provide benefits for particular conditions or subjects. Terpenes and/or essential oils can be employed in combination with each other, as well as in combination with cannabinoids, for example to target treatment of particular conditions. For example, terpinolene, terpineol and linalool or lavender, valerian and jasmine essential oils can be combined with cannabinoids or cannabis extract to act as a sleep aid or treat sleep disorders.

Alpha-pinene can be used as an anti-inflammatory, an antiangiogenic, an anti-ulcer agent, and a bronchodilator.

Linalool can be used for reducing anxiety, reducing inflammation (e.g., lung inflammation), to improve Alzheimer's disease or symptoms thereof, as a sedative, an analgesic, an anti-microbial, an antibacterial, and an anti-epileptic.

Myrcene can be used as an antibacterial, a neuroprotective agent, an antinociceptive, an analgesic, and to alleviate neuropathic pain, peptic ulcer disease, and inflammation. Depending on concentration, myrcene can be used as a sedative (e.g., over 0.5% myrcene) or to provide energizing effects (e.g., less than 0.5% myrcene).

Limonene can be used to reduce anxiety and depression, to dissolve cholesterol-containing gallstones, to neutralize gastric acid, support normal peristalsis, relieve heartburn and gastroesophageal reflux, to improve immune function, and as a chemopreventative against cancer.

Ocimene can be used as an antifungal agent, an antitumor agent, and a cyctotoxic agent.

Terpinolene can be used for antioxidant, mood regulation, central nervous system (CNS) regulation, anti-inflammatory, anti-diarrheal, anti-filarial, anti-fungal, antimalarial, anti-amoebic, anti-bacterial, cytotoxic, and anticancer effects.

Terpineol can be used to relax a subject, to aid digestion and improve gastrointestinal disorders, and to relieve influenza, bronchitis, cough, nasal congestion, and sinusitis.

Beta-caryophyllene can be used as an anti-inflammatory agent, an anti-tumor agent, and an analgesic.

Geraniol can be used to reduce or protect against neuropathy, as an antidepressant, to suppress angiogenesis, to improve anti-cancer agent efficacy, to suppress growth of cancer cells (e.g., lung cancer), as a chemopreventive against cancer, to reduce inflammation and apoptosis (e.g., in liver cells), to reduce oxidative stress, as an antioxidant, and as an antimicrobial.

Alpha-humulene can be used as an appetite suppressant, an anti-inflammatory agent, an insect repellant, an antibacterial, an antioxidant, and an allelopathic agent.

Phellandrene can be used as an antidepressant and an antihyperalgesic.

Carene can be used as an antioxidant, an antiproliferative, an antimicrobial, and to reduce excess body fluid production, such as of tears, mucous, or sweat.

Terpinene can be used as an antioxidant, an anti-inflammatory, an antimicrobial, an antiproliferative, to reduce oxidative stress, and to manage diabetes.

Fenchol can be used as an antibacterial agent, an antimycobacterial, an antimicrobial, and an antioxidant.

Borneol can be used to alleviate hyperalgesia, as a TRPA1 inhibitor, an anti-inflammatory agent, and an anti-nociceptive agent.

Bisabolol can be used as an anti-cancer agent, such as to induce apoptosis in leukemia, an anti-tumor agent (e.g., pancreatic cancer), and an antigenotoxicity agent.

Phytol can be used to relax a subject, such as by inhibiting degradation of GABA, as an anxiolytic, to resist menadione-induced oxidative stress, and as an antimicrobial.

Camphene can be used for pain relief, as an antioxidant, to induce apoptosis in cancer cells (e.g., melanoma), an antitumor agent, and an antibacterial.

Sabinene can be used as an antioxidant, an antimicrobial, an anticancer agent (e.g., oral, liver, lung, colon, melanoma, and leukemic cancer), to aid liver function, aid digestion, relieve arthritis, and relieve skin conditions.

Camphor can be used to improve skin healing (e.g., reconstructed human epidermis), as a local anesthetic, a muscle relaxant, an antipathogenic, and an antimicrobial agent.

Isoborneol can be used as an antioxidant, a cytotoxic, a DNA-protective, to inhibit herpes simplex virus type 1, and to inhibit HIV.

Menthol can be used as an analgesic, to desensitize α3β4 nicotinic acetylcholine receptors, as an antinociceptive, and as an anti-inflammatory agent.

Nerolidol can be used as an antifungal agent, an antimicrobial agent, an antioxidant, and an antimalarial agent.

Guaiol can be used as an antimicrobial agent, an antifungal agent, and an antibiotic.

Isopulegol can be used as a gastroprotective agent, an anti-inflammatory agent, to enhance permeability for transdermal administration of compounds, and to reduce the severity of seizures.

Geranyl acetate can be used as an antimicrobial agent, an antibacterial, and an antioxidant.

Cymene can be used as an anti-inflammatory agent, an anti-hyperalgesic, an antioxidant, an anti-diabetic, to aid in weight loss, to aid immune disorders, and to protect against acute lung injury.

Eucalyptol can be used as an antifungal agent, to alleviate inflammation (e.g., lung inflammation), an antioxidant, and an anticancer agent.

Pulegone can be used to enhance skin permeability, as an insecticide, and an antioxidant.

The compositions of the present disclosure can comprise one or more essential oils or essential oil compounds. Essential oils can include, but are not limited to: Linalool; B-Caryophyllene; B-Myrcene; D-Limonene; Humulene; a-Pinene; Ylang Ylang (*Cananga odorata*); Yarrow (*Achillea millefolium*); Violet (*Viola odorata*); Vetiver (*Vetiveria zizanoides*); Vanilla (*Vanilla plantifolia*); Tuberose (*Polianthes tuberosa*); Thyme (*Thymus vulgaris* L.); Tea Tree (*Melaleuca alternifolia*); Tangerine (*Citrus reticulata*); Spruce, Black (*Picea mariana*); Spruce (*Tsuga Canadensis*); Spikenard (*Nardostachys jatamansi*); Spearmint (*Mentha spicata*); Sandalwood (*Santalum spicatum*); Rosewood (*Aniba rosaeodora*); Rosemary Verbenone (*Rosmarinus officinalis*); Rosemary (*Rosmarinus officinalis*); Rose (*Rosa damascena*); Rose Geranium (*Pelargonium roseum*); Ravensara (*Ravensara aromatica*); Plai (*Zingiber cassumunar*) Pine Needle (*Pinus sylvestris* L.); Petitgrain (*Citrus aurantium*); Peppermint (*Mentha piperita*); Pepper, Black (*Piper nigrum* L.); Patchouli (*Pogostemon cablin*); Palo Santo (*Bursera graveolens*); Palmarosa (*Cymbopogon martini*); Osmanthus (*Osmanthus fragrans*); Oregano (*Origanum vulgare*); Orange, Sweet (*Citrus sinensis*); Oak Moss (*Evernia prunastri*); Nutmeg (*Myristica fragrans*) Niaouli (*Melaleuca viridifloria*); Neroli (aka Orange Blossom) (*Citrus aurantium*); Myrtle (*Myrtus communis*); Myrrh (*Commiphora myrrha); Mimosa (*Acacia decurrens*); Melissa (*Melissa officinalis* L.); Marjoram, Sweet (*Origanum majorana*); Manuka (*Leptospermum scoparium*); Mandarin, Red (*Citrus deliciosa*); Mandarin (*Citrus deliciosa*); Lotus, White (*Nelumbo nucifera*); Lotus, Pink (*Nelumbo nucifera*); Lotus, Blue (*Nelumbo nucifera*); Lime (*Citrus aurantifolia*); Lily (*Lilum aurantum*); Lemongrass (*Cymbopogon citratus*); Lemon (*Citrus limonum*); Lavender (*Lavandula angustifolium*); Lavandin (*Lavandula hybrida grosso*); Kanuka (*Kunzea ericoides*); Juniper Berry (*Juniperus cummunis*); Jasmine (*Jasminum officinale*); Jasmine Abs (*Jasminum sambac*); Helichrysum (*Helichrysum italicum*); Grapefruit, White (*Citrus×paradisi*); Grapefruit, Pink (*Citrus paradisi*); Ginger (*Zingiber officinalis*); Geranium (*Pelargonium graveolens*); Geranium, Bourbon (*Pelargonium graveolens*, 'Herit'); Gardenia (*Gardenia jasminoides*); Galbanum (*Ferula galbaniflua*); Frankincense (*Boswellia carterii*); Frangipani (*Plumeria alba*); Fir Needle White (*Abies alba*); Fir Needle Siberia (*Abies siberica*); Fir Needle Canada (*Abies balsamea*); Fennel, Sweet (*Foeniculum vulgare*); Eucalyptus Smithii. Eucalyptus Radiata, Eucalyptus Globulus, Eucalyptus Citriodora, Eucalyptus Blue Mallee (*Eucalyptus polybractea*); Elemi (*Canarium luzonicum*); Dill (*Anethum graveolens*); Cypress (*Cupressus sempervirens*); Cumin (*Cuminum cyminum*); Coriander (*Coriandum sativum*); Cocoa (*Theobroma cacao*); Clove (*Eugenia caryophylatta*); Clary Sage (*Salvia sclarea*); Cistus (aka *Labdanum*) (*Cistus ladaniferus* L.); Cinnamon (*Cinnamomum zeylanicum*); Chamomile, Roman (*Anthemis nobilis*); Chamomile, Blue (*Matricaria chamomilla*); Celery Seed (*Apium graveolins*); Cedarwood, Western Red (*Thuja plicata*); Cedarwood, Blood (*Juniperus virginiana*); Cedarwood Atlas (*Cedrus atlantica*); Carrot Seed (*Daucus carota*); Cardamon (*Elettaria cardamomum*); Caraway Seed (*Carum carvi*); Cajeput (*Melaleuca cajuputi*); Cade (*Juniperus oxycedrus*); Birch, White (*Betula alba*); Birch, Sweet (*Betula lenta*); Bergamot (*Citrus bergamia*); Bay Laurel (*Laurus nobilis*); Basil (*Ocimum basilicum*); Basil, Holy (*Ocimum sanctum*); Basil (*Ocimum basilicum*); Balsam Poplar (*Populus balsamifera*); Balsam Peru (*Myroxylon balsamum*); Angelica (*Angelica archangelica* L.); and combinations thereof.

The compositions of the present disclosure can comprise one or more additional ingredients, including but not limited to mushrooms or mushroom derivative products (e.g., reishi mushroom, chaga mushroom, maitake mushroom, oyster mushroom, cordyceps), maca (*Lepidium meyenii*), he sho wu (also he show wu or shou wu chih), superfoods or superfood derivative products (e.g., blueberries, acai berries, inca berries, goji berries, camucamu, coconut, lucuma, kale, cacao (e.g., cacao powder, cacao butter), sacha inchi, chia, flax, hemp, amaranth, quinoa, *moringa oleifera*), and combinations thereof.

Compounds used in compositions of the present disclosure can be extracted by a variety of methods. For example, extraction can be performed by maceration, infusion, decoction, percolation, Soxhlet extraction, pressurized solvent extraction, counter current extraction, ultrasonication, or supercritical fluid (e.g., carbon dioxide) extraction.

In some cases, compounds used in compositions of the present disclosure are extracted via supercritical fluid (e.g., carbon dioxide) extraction. For example, cannabinoid compounds can be extracted from hemp (e.g., hemp stalk and hemp stems) using supercritical carbon dioxide extraction.

The compositions of the present disclosure can comprise pregnenolone, including derivatives thereof. Pregnenolone can help protect a subject from cannabis intoxication, for example from THC. Pregnenolone or derivatives thereof can be formulated to be water soluble. A composition of the present disclosure can comprise between about 1 and 50 milligrams (mg) of pregnenolone or derivatives thereof. For example, a unit dosage of the present disclosure can comprise between about 1 and 50 milligrams (mg) of pregnenolone. Compositions of the present disclosure (e.g., unit dosages) can comprise about 1, 2, 3, 4, 5, 6, 7, 8, 9, 10, 15, 20, 25, 30, 35, 40, 45, or 50 mg of pregnenolone. Compositions of the present disclosure (e.g., unit dosages) can comprise at least about 1, 2, 3, 4, 5, 6, 7, 8, 9, 10, 15, 20, 25, 30, 35, 40, 45, or 50 mg of pregnenolone. Compositions of the present disclosure (e.g., unit dosages) can comprise at most about 1, 2, 3, 4, 5, 6, 7, 8, 9, 10, 15, 20, 25, 30, 35, 40, 45, or 50 mg of pregnenolone. Compositions comprising pregnenolone can be used in combination with any other compounds, ingredients, or formulations described herein, including esters, cyclodextrin complexes, microcapsules (e.g., sodium alginate microcapsules), immediate release formulations, delayed or extended release formulations, transbuccal formulations, and sublingual formulations.

Compositions of the present disclosure can be used to treat various diseases or conditions in subjects (e.g., humans, mammals, vertebrates), including but not limited to ALS, Alzheimer's, antibacterial resistant infections, anxiety, atherosclerosis, arthritis, asthma, cancer, colitis, Crohn's, diabetes, depression, endocrine disorders, epilepsy, seizures, fibromyalgia, glaucoma, heart disease, Huntington's, inflammation, irritable bowel syndrome (IBS), kidney disease, liver disease, motion sickness, nausea, neurodegeneration, neuropathic pain, neuropathy, obesity, obsessive compulsive disorder (OCD), osteoporosis, Parkinson's, prion diseases, Mad Cow disease, post-traumatic stress disorder (PTSD), rheumatism, schizophrenia, sickle cell anemia, skin conditions (e.g., psoriasis, dermatitis, allergic inflammation, chronic pruritus), sleep disorders (e.g., sleep-wake disorders, apnea), spinal cord injury, stress, stroke, and traumatic brain injury (TBI). The compositions of the present disclosure can be provided as a dry powder. For example, an oil-based composition (e.g., hemp oil) can be combined with a drying or powdering agent, such as cyclodextrin. In some cases, a powder composition can be provided on its own. In other cases, a powder composition can be provided in another product, such as a food product, cosmetic product, or other products and compositions such as those disclosed herein.

The compositions of the present disclosure can be provided in any suitable form, including but not limited to a liquid form, a gel form, a semi-liquid (e.g., a liquid, such as a viscous liquid, containing some solid) form, a semi-solid (a solid containing some liquid) form, or a solid form. Compositions can be provided in, for example, a tablet form, a capsule form, a food form a chewable form, a non-chewable form, a transbuccal form, a sublingual form, a slow-release form, a non-slow-release form, a sustained release form, or a non-sustained-release form.

The compositions of the present disclosure can be administered in any oral dosage form, including liquid dosage forms (e.g., a suspension or slurry), and oral solid dosage forms (e.g., a tablet or bulk powder). Tablets can include tablets, caplets, capsules, including soft gelatin capsules, and lozenges. Tablets can further comprise suitable binders, lubricants, diluents, disintegrating agents, colorants, flavoring agents, flow-inducing agents, and melting agents.

The compositions of the present disclosure can be administered transdermally, such as via a patch. The compositions of the present disclosure can be administered intravenously.

The compositions of the present disclosure can be administered topically. The compositions of the present disclosure can be administered via exposure to an aqueous solution, such as a subject immersing in a float tank. The compositions of the present disclosure can be formulated as a bath salt or liquid bath product, which can be dissolved or dispersed in water (e.g., a bath) for skin exposure, for example by immersion of the subject.

The compositions of the present disclosure can be provided as cosmetics or personal care products, such as soaps (e.g., solid, bar, liquid, or foaming), hand sanitizer, lotions, massage oils masks, makeup, moisturizers, sunscreen, toothpaste, mouth wash, or throat spray. Use of cannabinoids in such applications can provide benefits including reduction of inflammation in a subject.

The compositions of the present disclosure can be provided as a food composition in combination with a food carrier, including but not limited to food bars (e.g., granola bars, protein bars, candy bars), cereal products (e.g., oatmeal, breakfast cereals, granola), bakery products (e.g., bread, donuts, crackers, bagels, pastries, cakes), dairy products (e.g., milk, yogurt, cheese), beverages (e.g., milk-based beverages, sports drinks, fruit juices, teas, soft drinks, alcoholic beverages, bottled waters), beverage mixes, pastas, grains (e.g., rice, corn, oats, rye, wheat, flour), egg products, snacks (e.g., candy, chips, gum, gummies, lozenges, mints, chocolate), meats, fruits, vegetables or combinations thereof. Food compositions can comprise solid foods. Food compositions can comprise semi-solid foods. Food compositions can comprise liquid foods. A composition in a liquid form may be formulated from a dry mix, such as a dry beverage mix or a powder. A dry mix may be suitable in terms of transportation, storage, or shelf life. The composition can be formulated from the dry mix in any suitable manner, such as by adding a suitable liquid (e.g., water, milk, fruit juice, tea, or alcohol).

A food composition or food product can comprise a food bar, including but not limited to granola bars, protein bars, candy bars, and energy bars. A food composition or food product can comprise a cereal product, including but not limited to oatmeal, flour (e.g., wheat flour, rice flour, corn flour, barley flour), breakfast cereal, granola, bread, pasta, rice cakes, and popcorn. A food composition or food product can comprise a bakery product, including but not limited to bread, pastries, brownies, cakes, pies, donuts, crackers, and muffins. A food composition or food product can comprise a dairy product, including but not limited to milk, fermented milk, curd, whey, yogurt, cream, cheese, butter, clarified butter, ghee, and ice cream. A food composition or food product can comprise a nut butter or seed butter, including but not limited to peanut butter, almond butter, cashew butter, hazelnut butter, macadamia nut butter, pecan butter, pistachio butter, walnut butter, pumpkin seed butter, sesame seed butter, soybean butter, and sunflower seed butter. A food composition or food product can comprise an oil (e.g., a cooking oil), including but not limited to olive oil, coconut oil, vegetable oil, canola oil, corn oil, peanut oil, sunflower seed oil, almond oil, avocado oil, rice bran oil, cottonseed oil, flaxseed oil, linseed oil, grape seed oil, hemp oil, mustard oil, macadamia oil, palm oil, tea seed oil, walnut oil, margarine, lard, butter, clarified butter, ghee, or tallow. A food composition or food product can comprise sports food products such as energy gels, sports drinks, energy powders, energy bars, energy shots, protein powders, and protein drinks (e.g., protein shakes). A food composition or food product can comprise a beverage, including but not limited to water, electrolyte drinks, soda, coconut water, tea (e.g., Jun tea, black tea, green tea, white tea, herbal tea), coffee, a soft drink, an alcoholic beverage (e.g., cocktail, liquor, spirits, beer, wine, malt beverage), water, juice (e.g., apple juice, orange juice, tomato juice, vegetable juice, cranberry juice), a sports drink, electrolyte-enriched water, vitamin-enhanced water, a hangover-recovery drink, milk (e.g., dairy-based milk, coconut milk, almond milk, soy milk, hemp milk, rice milk, oat milk, cashew milk, hazelnut milk), and yogurt. A food composition or food product can comprise a fungus or fermented food or drink, including but not limited to kifir (kefir), jun, amasi, amazake, appam, ayran, doogh, bagoong, brem, cheonggukjang, chicha, kombucha, fermented bean curd, kimchi, lassi, miso, poi, yakult, and yogurt.

Compositions of the present disclosure can comprise pet or other animal products, such as animal food (e.g., dog food, cat food), treats, and nutritional supplements (e.g., liquids, sprays, or powders for application to food or water). These compositions can be formulated for or administered to domestic or pet animals (e.g., dogs, cats, small mammals, birds), livestock and other farm animals (e.g., cows, pigs, horses, sheep, goats), zoo animals, or any other vertebrates. Compositions for administration to animals can be formulated with microencapsulated cannabinoid-rich oil or non-encapsulated cannabinoid-rich oil, alone or in combination with essential oils, terpenes, and other components described herein. Compositions for administration to animals can be mixed into feed or water, prepared for spraying application (e.g., mixed in glycerin), for intravenous administration (e.g., in a syringe or an IV bag), in salves, vitamins, liquid vitamin pumps, treats, or other forms.

The compositions of the present disclosure can comprise an additional agent or agents, whether active or passive. Examples of such an agent include a sweetening agent, a flavoring agent, a coloring agent, a filling agent, a binding agent, a lubricating agent, an excipient, a preservative, or a manufacturing agent. Additional pharmaceutically acceptable excipients (in the case of pharmaceuticals) or other additives (for non-pharmaceutical applications) can be added to the composition. For example, if desired, any generally accepted soluble or insoluble inert pharmaceutical filler (diluent) material can be included in the final product (e.g., a solid dosage form). Such inert pharmaceutical filler can comprise a monosaccharide, a disaccharide, a polyhydric alcohol, inorganic phosphates, sulfates or carbonates, and combinations thereof. Examples of suitable inert pharmaceutical fillers include sucrose, dextrose, lactose, xylitol, fructose, sorbitol, calcium phosphate, calcium sulfate, calcium carbonate, microcrystalline cellulose, and combinations thereof. An effective amount of any generally accepted pharmaceutical lubricant, such as calcium or magnesium soaps, can be added.

The compositions of the present disclosure can be administered to a subject. Compositions can be administered in a variety of ways, including but not limited to oral and topical administration.

Administering the compositions of the present disclosure to a subject can provide one or more beneficial effects. Beneficial effects can include but are not limited to pain relief, reduced bacterial growth, reduced blood sugar levels, improved blood lipid and cholesterol profiles, increased fat burning, reduced appetite, stimulated appetite, reduced vomiting or nausea, reduced seizures or convulsions, antifungal effects, reduced inflammation, reduced arthritis (e.g., rheumatoid arthritis), reduced insomnia or aided sleep, reduced arterial blockage, inhibited cancer cell growth, improved psoriasis, tranquilizing effects, antispasmodic effects, reduced anxiety, bone growth promotion, reduced intestinal contractions, and nervous system protection.

Any of the subject compositions can be provided in a unit dosage form. A unit dosage is an amount of a compound, such as a cannabinoid compound delivered alone or in combination with other components, which is to be administered to a subject at or about one time point. Other components which can be included with a unit dosage include but are not limited to cosmetics, food carriers, food bars, baked goods, dairy products, oils, beverages, solid dosages (e.g., tablets), or liquid dosages. A unit dosage of a cannabinoid compound can be about 10, 20, 30, 40, 50, 60, 70, 80, 90, 100, 125, 150, 175, 200, 250, 300, 350, 400, 450, 500, 600, 700, 800, 900, 1000 or more milligrams (mg). A unit dosage of a cannabinoid compound can be at least about 10, 20, 30, 40, 50, 60, 70, 80, 90, 100, 125, 150, 175, 200, 250, 300, 350, 400, 450, 500, 600, 700, 800, 900, 1000 or more milligrams (mg). A unit dosage of a cannabinoid compound can be at most about 10, 20, 30, 40, 50, 60, 70, 80, 90, 100, 125, 150, 175, 200, 250, 300, 350, 400, 450, 500, 600, 700, 800, 900, 1000 or more milligrams (mg). A unit dosage can be an hourly dosage. A unit dosage can be a daily dosage. A unit dosage can provide about $1/24$, $1/12$, $1/8$, $1/6$, $1/4$, $1/3$, $1/2$, or all of a daily dosage of one or more cannabinoids for a subject. A unit dosage can take the form of a tablet, gel, liquid, food product, food bar, container of liquid of defined volume, or other forms described herein, packaged for one-time consumption or administration.

The compositions described herein can provide several advantages, including but not limited to increased shelf stability, increased bioavailability, increased bioactivity, and delayed release. The compositions described herein, when administered to a subject, can have various release profiles, half-lives, and metabolic characteristics. The subject compositions can comprise a plurality of microcapsules, wherein an individual microcapsule in the plurality is characterized by exhibiting at least one of: (a) a sigmoidal release profile of the at least one cannabinoid compound; (b) a plasma half-life of the at least one cannabinoid compound greater than twice that of the at least one cannabinoid compound in non-encapsulated form; (c) a first pass metabolism of the at least one cannabinoid compound reduced by at least 50% compared to the at least one cannabinoid compound in non-encapsulated form; d) a rate of excretion of the at least one cannabinoid compound from a subject's body reduced by at least 20% compared to the at least one cannabinoid compound in non-encapsulated form; or (e) a degradation rate at an ambient temperature of at least 20° C. of the at least one cannabinoid compound of less than about 50% of a degradation rate of the at least one cannabinoid compound in non-encapsulated form.

The compositions described herein can have a shelf half-life of at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 110, 120, 130, 140, 150, 160, 170, 180, 190, 200, 210, 240, 270, 300, 330, or 360 days. In some cases, the compositions described herein can have a shelf half-life of at least about 1, 2, 3, 4, or 5 years. Compositions in microencapsulated form can be characterized by a cannabinoid degradation rate at an ambient temperature of at least 20° C. of at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% less than the degradation rate of a non-encapsulated cannabinoid composition.

Cannabinoid compositions in microencapsulated form can be characterized by a plasma half-life in a subject of at least 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.5, 4.0, 4.5, or 5.0 times that of a non-encapsulated cannabinoid composition. Plasma half-life of a composition can be determined experimentally by administering the composition to a subject, taking plasma samples from a subject at multiple time points, and measuring the concentration of the compound or compounds of interest in those plasma samples. The concentration of the compound or compounds of interest will reach a peak value in the plasma, then fall as the compound or compounds are metabolized, degraded, or cleared from the blood stream. The plasma half-life is the time for the plasma concentration value to be halved.

The cannabinoid release profile can be sigmoidal (e.g., having an 'S' shape curve, such as a logistic function). The cannabinoid release profile can be non-sigmoidal. The cannabinoid release profile can be linear. The cannabinoid release profile can be non-linear. The cannabinoid release profile can be instant release. The cannabinoid release profile can be non-instant release. The cannabinoid release profile can be delayed release. The cannabinoid release profile can be constant or sustained release. The cannabinoid release profile can be non-constant or non-sustained release.

Tablets can be formulated in sustained release format. Methods of making sustained release tablets are known in the art; see, for example, U.S. Patent Publication No. 2006/0051416 and U.S. Patent Publication No. 2007/0065512. Gradual-release tablets are known in the art; examples of such tablets are set forth in U.S. Pat. No. 3,456,049, for example. A slow- or sustained-release form may delay disintegration or absorption of the composition or one or more components thereof.

In some cases, no more than 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% of a cannabinoid compound is released from a microcapsule within 1 hour of administration to a subject. In some cases, no more than 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% of a cannabinoid compound is released from a microcapsule within 2 hours of administration to a subject. In some cases, no more than 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% of a cannabinoid compound is released from a microcapsule within 3 hours of administration to a subject. In some cases, no more than 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% of a cannabinoid compound is released from a microcapsule within 4 hours of administration to a subject. In some cases, no more than 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% of a cannabinoid compound is released from a microcapsule within 5 hours of administration to a subject. In some cases, no more than 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% of a cannabinoid compound is released from a microcapsule within 6 hours of administration to a subject. In some cases, no more than 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% of a cannabinoid compound is released from a microcapsule within 7 hours of administration to a subject. In some cases, no more than 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% of a cannabinoid compound is released from a microcapsule within 8 hours of administration to a subject.

A release profile is the relationship between time and the amount of a compound released into a subject or the concentration of the compound within the subject (e.g., within the plasma). Release profiles can be measured in a similar manner to plasma half-life. A composition can be administered to a subject, and samples (e.g., plasma samples or blood samples) can be taken from the subject at multiple time points. The concentration of the compound or compounds of interest can be measured in those samples, and a release profile can be plotted.

Compounds taken up into a subject via the gastrointestinal system can be transported to the liver before entering general circulation. Compounds susceptible to metabolic degradation in the liver can have their activities substantially reduced by the first-pass metabolism through the liver. Encapsulation (e.g., microencapsulation) of compounds can reduce first-pass metabolism of the compounds in the liver. Compositions in microencapsulated form can be characterized by a first pass cannabinoid metabolism in a subject of at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% less than that of a non-encapsulated cannabinoid composition. Compositions in microencapsulated form can be characterized by a cannabinoid excretion rate from a subject of at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% less than that of a non-encapsulated cannabinoid composition.

The compositions described herein, when administered to a subject, can have improved bioavailability, bioactivity, or both. Bioavailability is the fraction of an administered dosage of unchanged compound that reaches systemic circulation. Cannabinoid compositions in microencapsulated form can be characterized by a bioavailability in a subject of at least 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.5, 4.0, 4.5, 5.0, 5.5, 6.0, 6.5, 7.0, 7.5, 8.0, 8.5, 9.0, 9.5, or 10.0 times that of a non-encapsulated cannabinoid composition. Cannabinoid compositions in microencapsulated form can be characterized by a bioavailability in a subject of at least 5%, 10%, 15%, 20%, 25%, 30%, 35%, 40%, 45%, 50%, 55%, 60%, 65%, 70%, 75%, 80%, 85%, 90%, 95%, 96%, 97%,%, 98%, 99%, or 100%. Bioactivity, or biological activity, is the activity exerted by the active ingredient or ingredients in a composition. Cannabinoid compositions in microencapsulated form can be characterized by a bioactivity in a subject of at least 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.5, 4.0, 4.5, 5.0, 5.5, 6.0, 6.5, 7.0, 7.5, 8.0, 8.5, 9.0, 9.5, or 10.0 times that of a non-encapsulated cannabinoid composition.

Subjects of the present disclosure can include humans and other animals, such as pets (e.g., dogs, cats, birds, small mammals, snakes) and livestock or farm animals (e.g., cows, pigs, horses, sheep, chickens). Compositions of the present disclosure can be useful for veterinary applications.

Methods and systems of the present disclosure may be used for forming compositions for various uses, such as encapsulating compositions (e.g., therapeutics compositions). Examples of uses of methods of the present disclosure are provided in WO/2016/094810, which is entirely incorporated herein by reference.

EXAMPLES

Example 1—Microencapsulation of Cannabinoids

A hemp oil composition is produced, comprising cannabinoids including cannabidiol. Additional essential oils are added to the composition. Alginate (e.g., sodium alginate) and quillaja tree extract are added to the composition. The composition is microencapsulated via a microfluidic nozzle device. Calcium chloride is used to cross-link the microcapsules. The microcapsules are packaged in a suspension, transported, and sold.

Example 2—Administration of Cannabinoid Composition to a Subject

A cannabinoid composition, such as the microencapsulated cannabinoid composition described in Example 1, is administered to a subject suffering from a cannabinoid deficiency related condition. The level of cannabinoids in the subject increases, and the condition is improved.

Example 3—Cannabidiol-Rich Hemp and Coconut Oil Product

Hempseed oil is enriched in cannabidiol compounds by addition of hemp stalk and stem extract containing 10% to 40% cannabidiol compounds by weight. The enriched hempseed oil is blended into coconut oil to produce a final composition of about 100 milligrams of cannabidiol compounds in 8 fluid ounces of coconut oil. The coconut oil product is then used to produce consumer products such as moisturizers, lotions, cooking oils, smoothies, spreads, and other food products.

Example 4—Cannabidiolic Acid-Rich Hemp and Coconut Oil Product

Hempseed oil is enriched in cannabidiolic acid by addition of hemp stalk and stem extract containing 10% to 40% cannabidiolic acid by weight. The enriched hempseed oil is blended into coconut oil to produce a final composition of about 100 milligrams of cannabidiolic acid in 8 fluid ounces of coconut oil. The coconut oil product is then used to produce consumer products such as moisturizers, lotions, cooking oils, smoothies, spreads, and other food products.

Example 5—Cannabidiol-Rich Hot Chocolate Mix

Hempseed oil is enriched in cannabidiol compounds by addition of hemp stalk and stem extract containing 10% to 40% cannabidiol compounds. Hempseed oil rich in cannabidiol compounds is then combined with cyclodextrin (e.g., certified organic cyclodextrin) to form a dry powder. The hemp oil powder is mixed with powdered cacao, cacao butter mix, sweeteners, and optionally superfood products such as reishi mushroom powder, chaga mushroom powder, maca, or he shou wu. The mixture is packaged and sold as a chocolate beverage mix (e.g., hot chocolate mix).

Example 6—Production and Packaging of Cannabinoid-Rich Product

A standardized supercritical carbon dioxide extract of hemp stalk and stem is extracted. The extract (e.g., a paste) is blended into hemp seed oil. The blend of hemp extract and hemp oil is prepared with a THC content below 0.3%, and with CBD content of about 10-40% by weight. The hemp extract and hemp oil blend is further blended into coconut oil to provide about 100 mg of CBD per 8 ounce of coconut oil (about 423 milligrams per liter). The coconut oil blend with CBD is packaged (e.g., in a jar) and sold to a consumer.

Example 7—Administration of Pregnenolone Composition to a Subject

A cannabinoid and pregnenolone composition, such as the microencapsulated cannabinoid composition described in Example 1 further comprising pregnenolone (e.g., 1-50 mg of pregnenolone), is administered to a subject suffering from cannabinoid intoxication or addiction. The subject is protected from CB1 receptor overactivation, and the condition is improved.

Example 8—Preparation of Microencapsulated Composition

Formulations comprising quillaja extract (e.g., Q Natural), hemp oil, water, and optionally sodium alginate were prepared using a microfluidic fluid processor (e.g., Microfluidizer from Microfluidics/IDEX Corporation). Formulations were prepared as described in Table 1. Test 1 was prepared with 60 g of quillaja extract (e.g., Q Natural), 80 g of hemp oil, and 100 g of water, at an operating pressure of 30,000 psi in the microfluidic fluid processor. Test 2 was prepared with 10 g of quillaja extract (e.g., Q Natural), 15 g of hemp oil, 198 g of water, and 2 g of sodium alginate, at an operating pressure of 30,000 psi in the microfluidic fluid processor.

After processing in the microfluidic fluid processor, particle size distribution was analyzed using a laser diffraction particle size analyzer (e.g., Horiba LA950). Optical microscope images were also taken.

Three passes each of Test 1 and Test 2 were conducted, and the tenth percentile (D10), fiftieth percentile (D50), and ninetieth percentile (D90) particle sizes are reported in Table 1. Particle sizes were also analyzed for an unprocessed solution (Test 1, Pass 0).

TABLE 1

Formulation and size distribution information for microencapsulated compositions.

| Test | Pass # | Pressure | Q Natural | Hemp Oil | Water | Sodium alginate | D10 (μm) | D50 (μm) | D90 (μm) |
|---|---|---|---|---|---|---|---|---|---|
| 1 | 0 | 30,000 psi | 60 g | 80 g | 100 g | — | 1.9737 | 7.117 | 35.703 |
|  | 1 |  |  |  |  | — | 0.0768 | 0.1296 | 0.2881 |
|  | 2 |  |  |  |  | — | 0.0697 | 0.1096 | 0.1791 |
|  | 3 |  |  |  |  | — | 0.0929 | 0.1405 | 0.2202 |
| 2 | 1 | 30,000 psi | 10 g | 15 g | 198 g | 2 g | 0.1171 | 0.1965 | 2.0719 |
|  | 2 |  |  |  |  |  | 0.0688 | 0.1097 | 0.2209 |
|  | 3 |  |  |  |  |  | 0.099 | 0.1583 | 1.3443 |

FIG. 1A shows a 400× magnification micrograph image of an unprocessed quillaja extract, hemp oil, and water composition (Test 1, Pass 0), with a 50 μm scale bar. FIG. 1B shows a 1000× magnification micrograph image of an unprocessed quillaja extract, hemp oil, and water composition (Test 1, Pass 0), with a 50 μm scale bar.

Figure 2A:
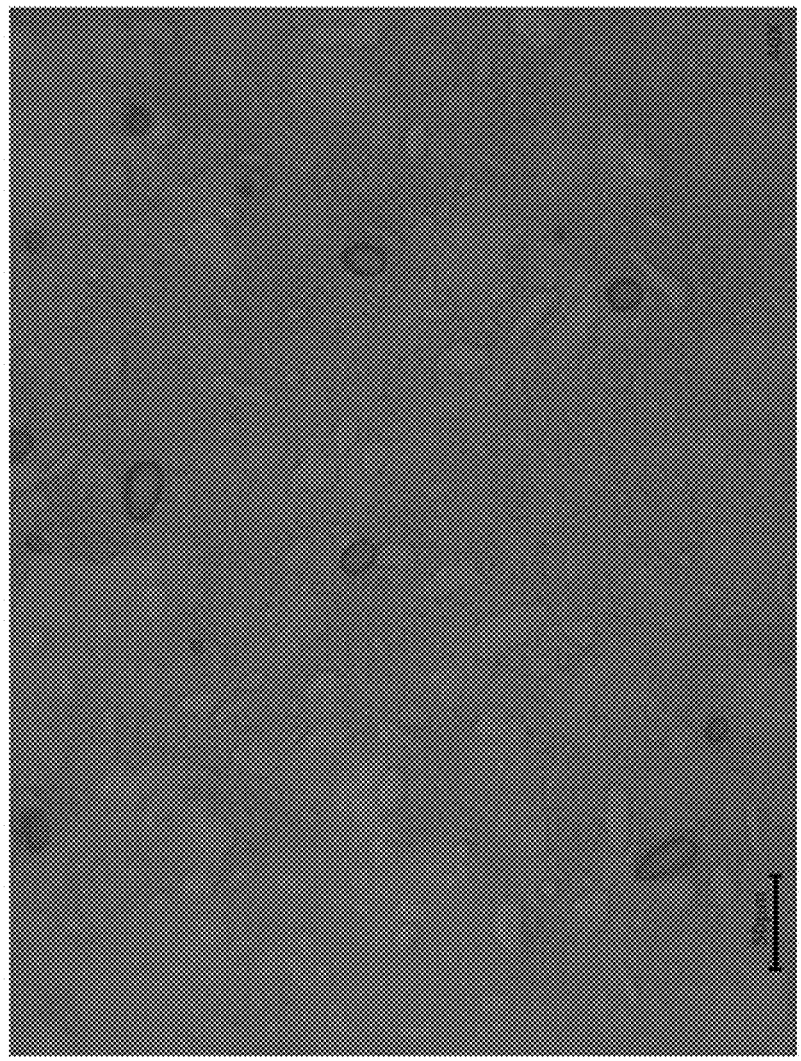
FIG. 2A shows an exemplary microscope image of an unprocessed composition of quillaja extract, hemp oil, and water at 400× magnification.
Figure 2B:
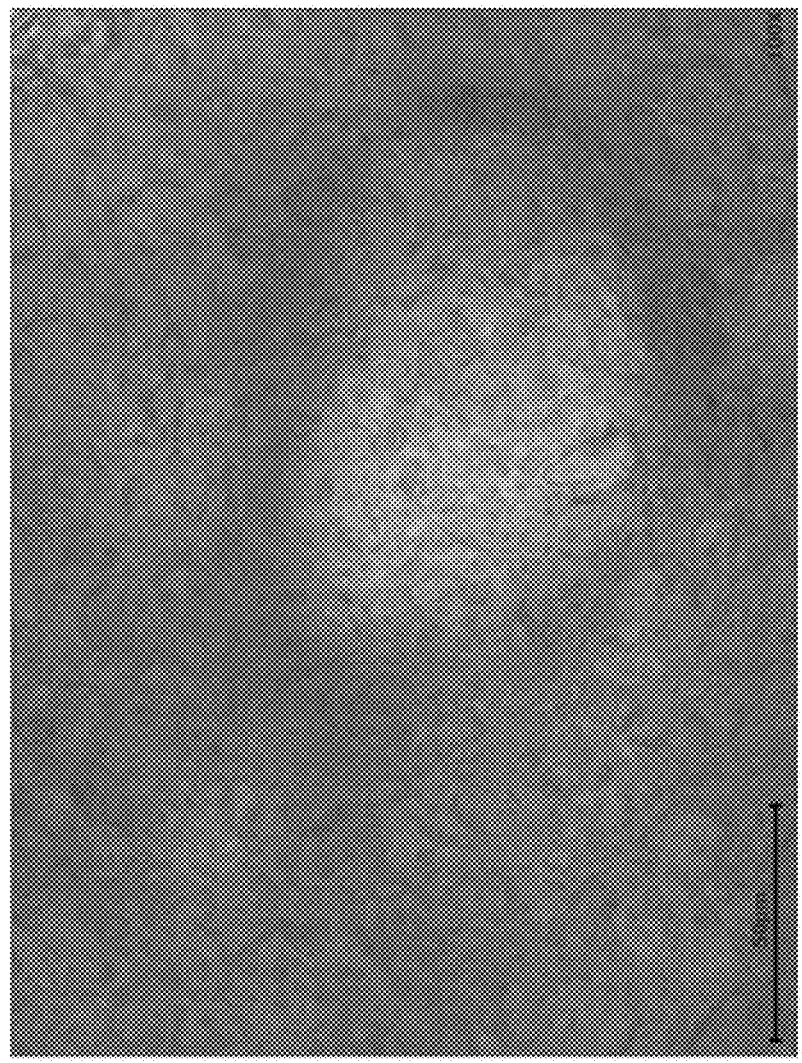
FIG. 2B shows an exemplary microscope image of an unprocessed composition of quillaja extract, hemp oil, and water at 1000× magnification.

FIG. 2A shows a 400× magnification micrograph image of a quillaja extract, hemp oil, and water composition (Test 1, Pass 1), with a 50 μm scale bar. FIG. 2B shows a 400× magnification micrograph image of a quillaja extract, hemp oil, and water composition (Test 1, Pass 2), with a 50 μm scale bar. FIG. 2C shows a 1000× magnification micrograph image of a quillaja extract, hemp oil, and water composition (Test 1, Pass 2), with a 10 μm scale bar. FIG. 2D shows a 1000× magnification micrograph image of a quillaja extract, hemp oil, and water composition (Test 1, Pass 3), with a 10 μm scale bar.

Figure 3A:
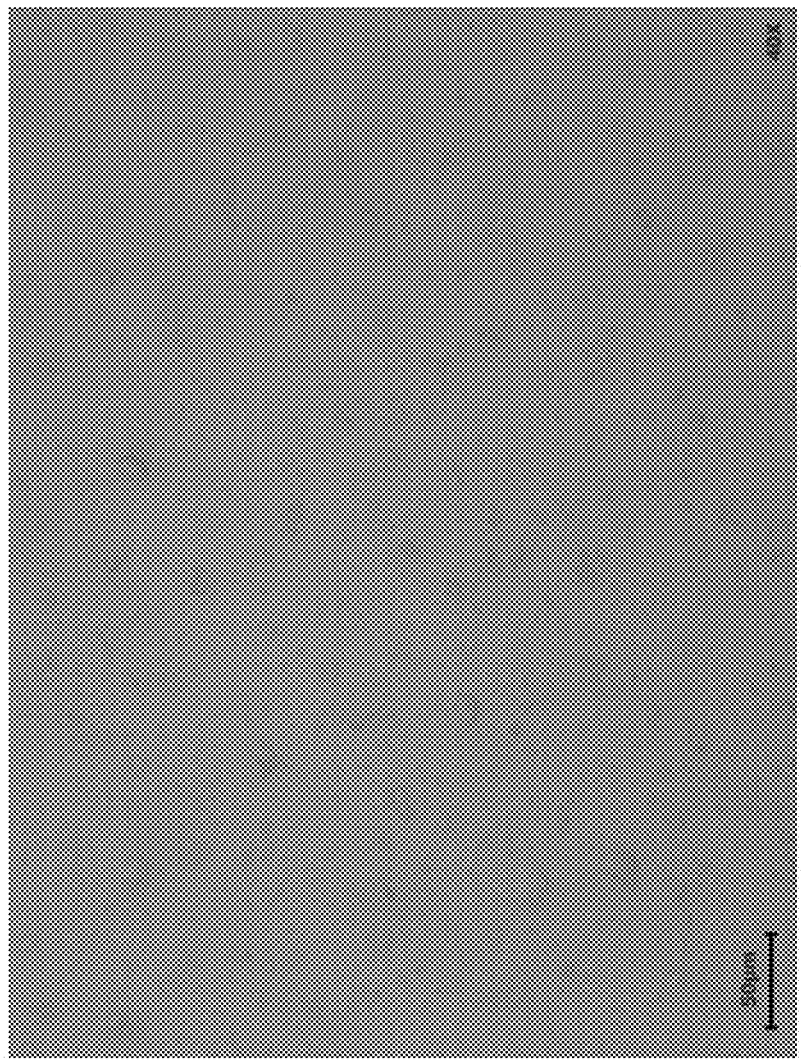
FIG. 3A shows an exemplary microscope image of a microfluidic processed composition of quillaja extract, hemp oil, and water at 400× magnification.
Figure 3B:
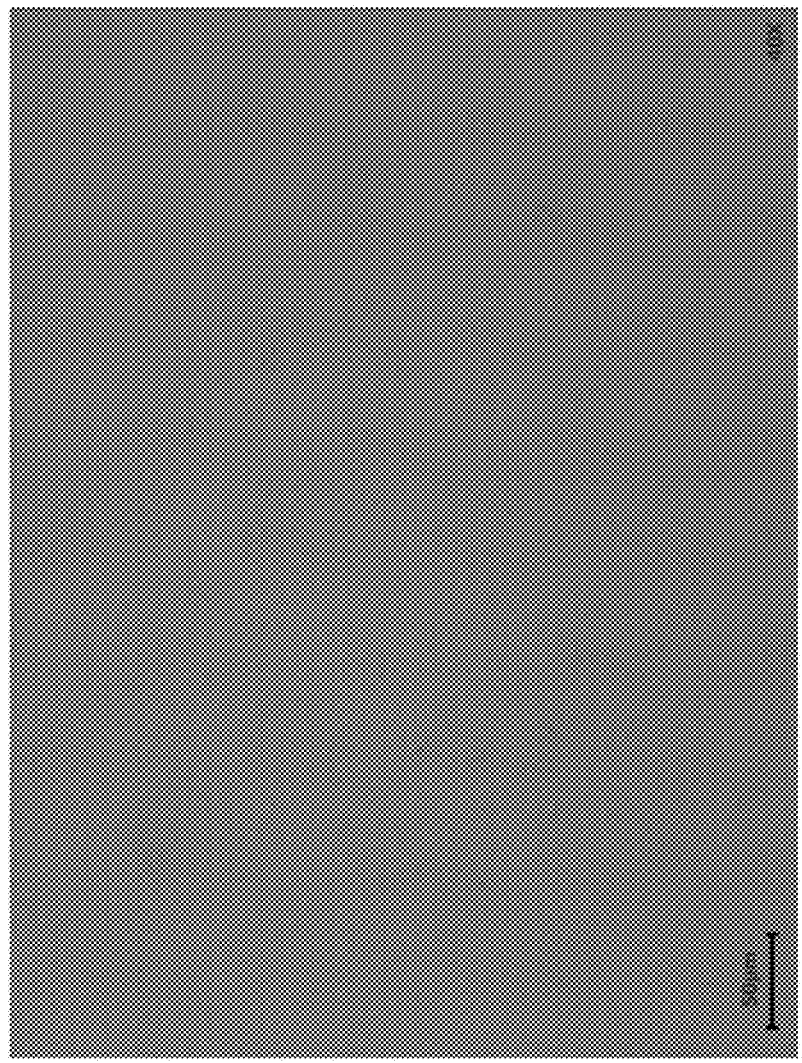
FIG. 3B shows an exemplary microscope image of a microfluidic processed composition of quillaja extract, hemp oil, and water at 400× magnification.
Figure 3C:
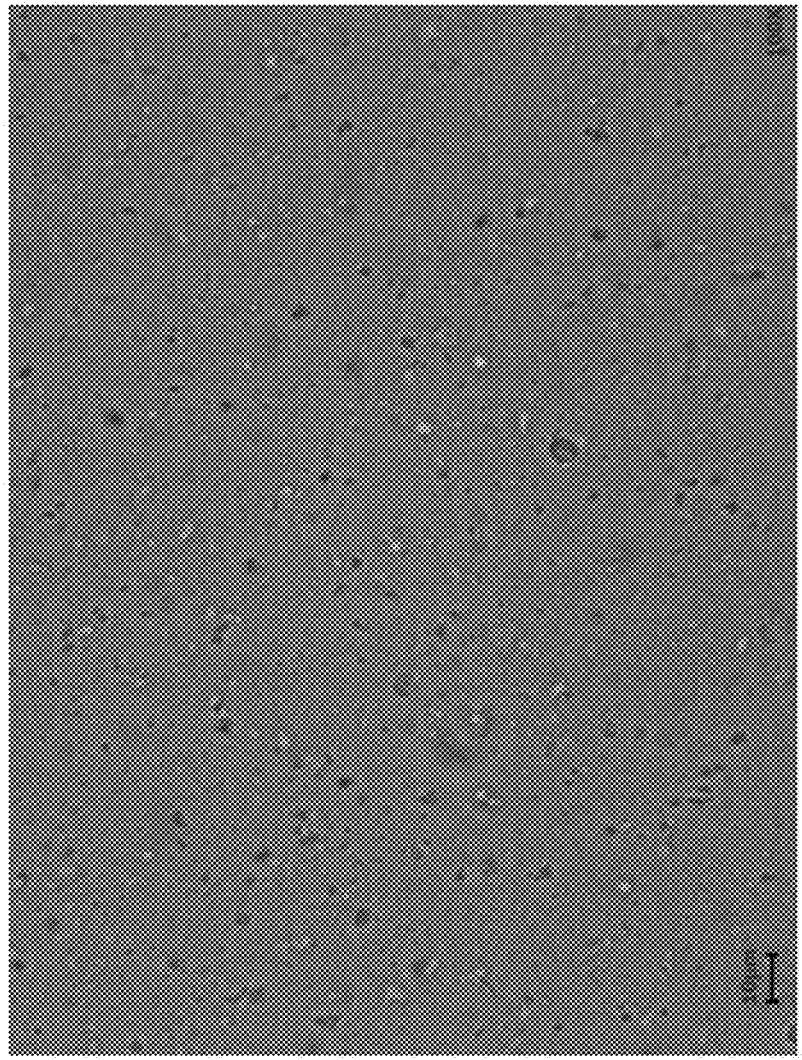
FIG. 3C shows an exemplary microscope image of a microfluidic processed composition of quillaja extract, hemp oil, and water at 1000× magnification.
Figure 3D:
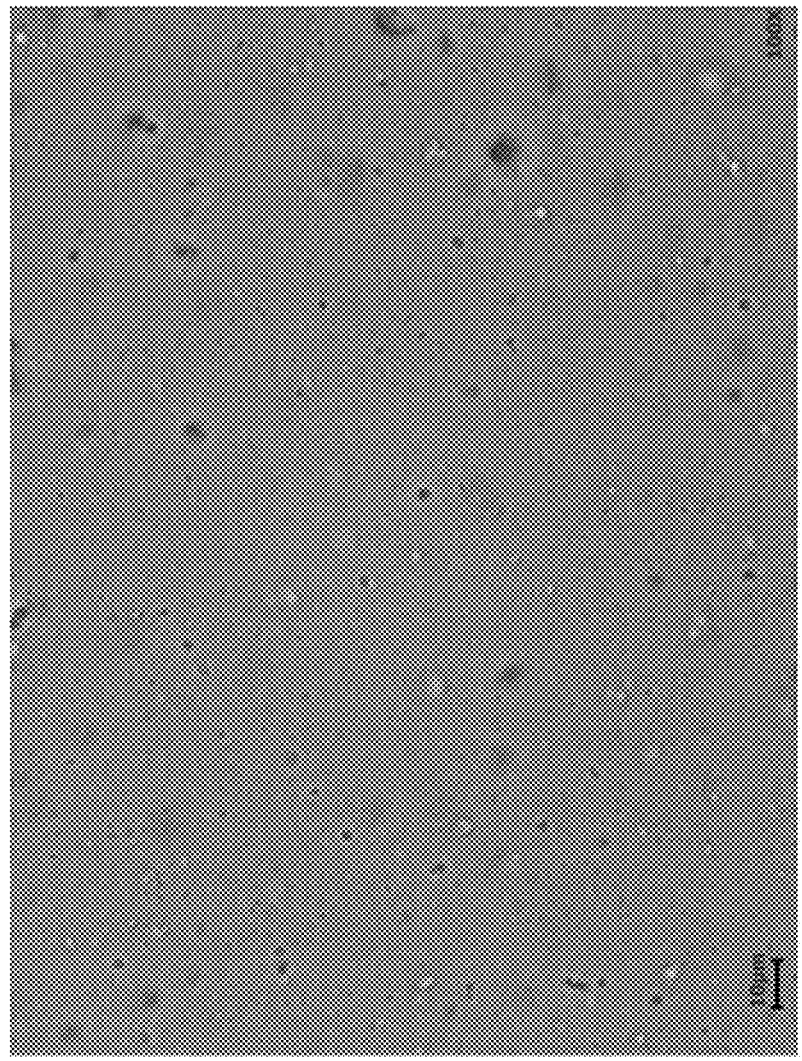
FIG. 3D shows an exemplary microscope image of a microfluidic processed composition of quillaja extract, hemp oil, and water at 1000× magnification.
Figure 4A:
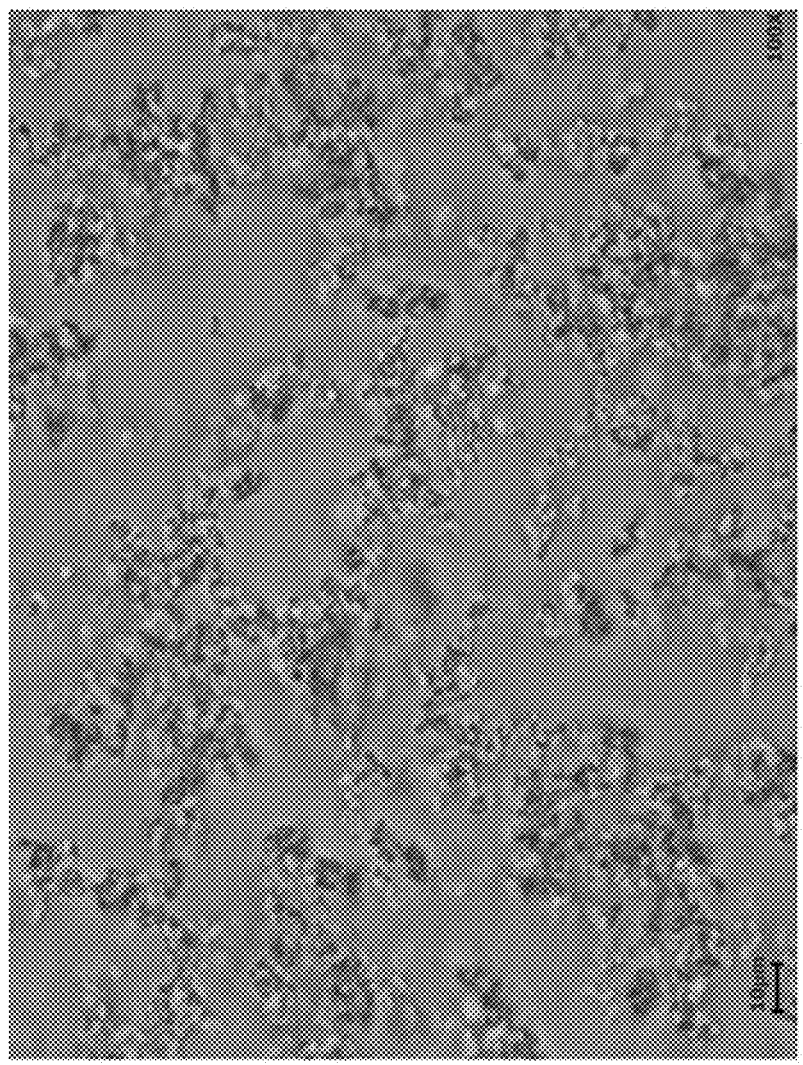
FIG. 4A shows an exemplary microscope image of a microfluidic processed composition of quillaja extract, hemp oil, water, and sodium alginate at 1000× magnification.
Figure 4B:
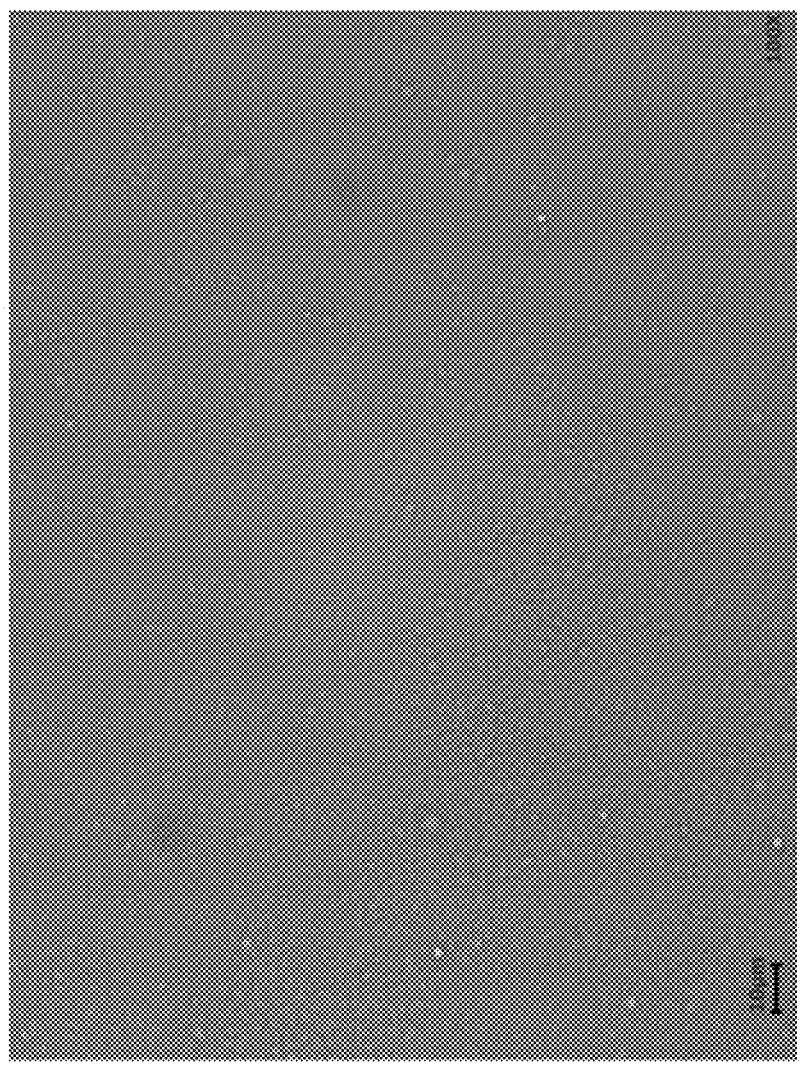
FIG. 4B shows an exemplary microscope image of a microfluidic processed composition of quillaja extract, hemp oil, water, and sodium alginate at 1000× magnification.
Figure 4C:
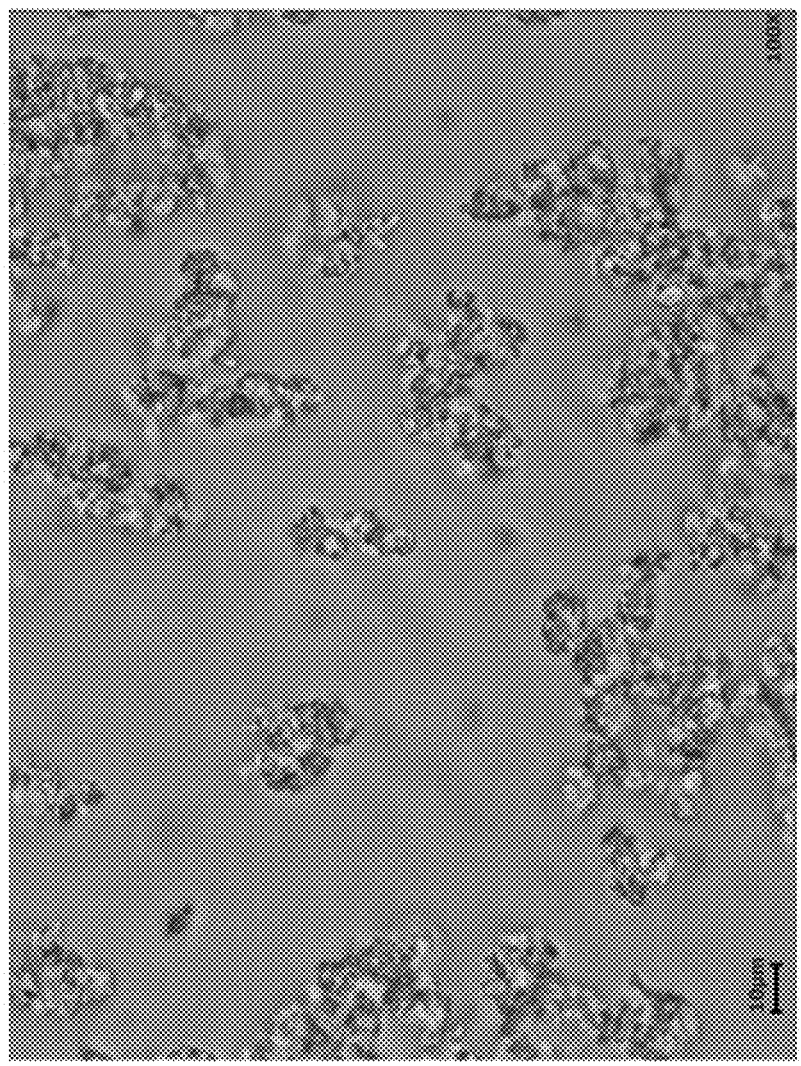
FIG. 4C shows an exemplary microscope image of a microfluidic processed composition of quillaja extract, hemp oil, water, and sodium alginate at 1000× magnification.

FIG. 3A shows a 1000× magnification micrograph image of a quillaja extract, hemp oil, water, and sodium alginate composition (Test 2, Pass 1), with a 10 μm scale bar. FIG. 3B shows a 1000× magnification micrograph image of a quillaja extract, hemp oil, water, and sodium alginate composition (Test 2, Pass 2), with a 10 μm scale bar. FIG. 3C shows a 1000× magnification micrograph image of a quillaja extract, hemp oil, water, and sodium alginate composition (Test 2, Pass 3), with a 10 μm scale bar.

What is claimed is:

1. An emulsion comprising a plurality of droplets, wherein a droplet of said plurality of droplets has a size less than or equal to about 1 micrometer, and comprises one or more compositions comprising at least one cannabinoid compound, and
    wherein said droplet is characterized by one or more members selected from the group consisting of: (i) a sigmoidal release profile of said one or more compositions, (ii) a plasma half-life of said one or more compositions greater than that of said one or more compositions in non-encapsulated form, (iii) a first pass metabolism of said one or more compositions reduced by at least 5% compared to said one or more compositions in non-encapsulated form, (iv) a rate of excretion of said one or more compositions from a subject's body reduced by at least 5% compared to said one or more compositions in non-encapsulated form, and (v) a degradation rate at an ambient temperature of at least 20° Celsius (° C.) of said one or more compositions of at least 5% less than a degradation rate of said one or more compositions in non-encapsulated form.

2. The emulsion of claim 1, wherein said emulsion is water soluble.

3. The emulsion of claim 1, wherein said emulsion has a shelf half-life of at least 1 week.

4. The emulsion of claim 1, wherein said droplet is characterized as having said first pass metabolism reduced by at least 30% compared to said one or more compositions in non-encapsulated form.

5. The emulsion of claim 1, wherein said droplet is characterized as having said rate of excretion reduced by at least 10% compared to said one or more compositions in non-encapsulated form.

6. The emulsion of claim 1, wherein said droplet is characterized as having said degradation rate at an ambient temperature of at least 20° C. of said one or more compositions of at least 20% less than said degradation rate of said one or more compositions in non-encapsulated form.

7. The emulsion of claim 1, wherein said one or more compositions in said droplet has a bioavailability of at least twice that of said one or more compositions in non-droplet-encapsulated form.

8. The emulsion of claim 1, wherein said droplet has a size less than or equal to about 500 nanometers.

9. The emulsion of claim 8, wherein said droplet has a size between about 10 nanometers and about 200 nanometers.

10. The emulsion of claim 1, wherein said one or more compositions further comprise at least one agent selected from the group consisting of: an herb, an essential oil, a therapeutic compound, a food product, a mushroom, pregnenolone, fulvic acid, L-Theanine, Fish Oil, phenyl ethyl amine (PEA), tulsi, lemon balm, passion flower, blue lotus, cacao, maca, schizandra, Siberian ginseng, kava, skullcap, valerian, hops, California poppy, catuba, epidmedium, pao d'arco, ashwaganda, ginko, albiza, reishi, lion's mane, maitake, chaga, vitamin C, turmeric, tetrahydrocannabinol (THC), bioperine, and xanthohumol.

11. The emulsion of claim 1, wherein said droplet has a tetrahydrocannabinol (THC) content of at most 5%.

12. The emulsion of claim 1, wherein said one or more compositions further comprise at least one terpene compound.

13. The emulsion of claim 1, wherein said at least one cannabinoid compound comprises cannabidiol (CBD).

14. The emulsion of claim 1, further comprising a surfactant.

15. The emulsion of claim 14, wherein said surfactant is a natural surfactant or a natural oil.

16. The emulsion of claim 15, wherein said natural surfactant is selected from a group consisting of saponin, xylitol, and seed hull extract.

17. The emulsion of claim 1, wherein said emulsion further comprises a stabilizer.

18. The emulsion of claim 17, wherein said stabilizer is alginate.

19. The emulsion of claim 1, wherein said plurality of droplets has a polydispersity index of less than about 10.

20. The emulsion of claim 19, wherein said plurality of droplets has a polydispersity index of less than about 5.

21. The emulsion of claim 1, wherein said droplet is characterized by at least two members selected from the group consisting of (i) a sigmoidal release profile of said one or more compositions, (ii) a plasma half-life of said one or more compositions greater than that of said one or more compositions in non-encapsulated form, (iii) a first pass metabolism of said one or more compositions reduced by at least 5% compared to said one or more compositions in non-encapsulated form, (iv) a rate of excretion of said one or more compositions from a subject's body reduced by at least 5% compared to said one or more compositions in non-encapsulated form, and (v) a degradation rate at an ambient temperature of at least 20° Celsius (° C.) of said one or more compositions of at least 5% less than a degradation rate of said one or more compositions in non-encapsulated form.

* * * * *